(12) United States Patent
Abbott

(10) Patent No.: US 8,162,963 B2
(45) Date of Patent: Apr. 24, 2012

(54) ANGLED ANASTOMOSIS DEVICE, TOOLS AND METHOD OF USING

(75) Inventor: Ryan C. Abbott, San Jose, CA (US)

(73) Assignee: Maquet Cardiovascular LLC, San Jose, CA (US)

( * ) Notice: Subject to any disclaimer, the term of this patent is extended or adjusted under 35 U.S.C. 154(b) by 821 days.

(21) Appl. No.: 10/872,071

(22) Filed: Jun. 17, 2004

(65) Prior Publication Data

US 2005/0283173 A1    Dec. 22, 2005

(51) Int. Cl.
*A61B 17/08* (2006.01)
(52) U.S. Cl. .................................................... 606/153
(58) Field of Classification Search .......... 606/153–157, 606/108, 200, 213
See application file for complete search history.

(56) References Cited

U.S. PATENT DOCUMENTS

| | | |
|---|---|---|
| 3,254,650 A | 6/1966 | Collito |
| 3,254,651 A | 6/1966 | Collito |
| 3,519,187 A | 7/1970 | Kapitanov et al. |
| 3,774,615 A | 11/1973 | Lim et al. |
| 4,118,806 A | 10/1978 | Porier et al. |
| 4,214,587 A | 7/1980 | Sakura, Jr. |
| 4,217,664 A | 8/1980 | Faso |
| 4,350,160 A | 9/1982 | Kolesov et al. |
| 4,352,358 A | 10/1982 | Angelchik |
| 4,366,819 A | 1/1983 | Kaster |
| 4,368,736 A | 1/1983 | Kaster |
| 4,503,568 A | 3/1985 | Madras |
| 4,523,592 A | 6/1985 | Daniel |
| 4,553,542 A | 11/1985 | Schenck et al. |
| 4,589,416 A | 5/1986 | Green |
| 4,593,693 A | 6/1986 | Schenck |
| 4,607,637 A | 8/1986 | Berggren et al. |
| 4,624,255 A | 11/1986 | Schenck et al. |
| 4,624,257 A | 11/1986 | Berggren et al. |
| 4,657,019 A | 4/1987 | Walsh et al. |
| 4,665,906 A | 5/1987 | Jervis |
| 4,721,109 A | 1/1988 | Healey |
| 4,747,407 A | 5/1988 | Liu et al. |
| 4,752,024 A | 6/1988 | Green et al. |
| 4,861,330 A | 8/1989 | Voss |
| 4,883,453 A | 11/1989 | Berry et al. |
| 4,892,098 A | 1/1990 | Sauer |
| 4,907,591 A | 3/1990 | Vasconcellos et al. |
| 4,917,087 A | 4/1990 | Walsh et al. |
| 4,917,090 A | 4/1990 | Berggren et al. |
| 4,917,091 A | 4/1990 | Berggren et al. |
| 4,930,674 A | 6/1990 | Barak |
| 4,997,439 A | 3/1991 | Chen |
| 5,005,749 A | 4/1991 | Aranyi |
| 5,015,238 A | 5/1991 | Solomon et al. |
| 5,062,842 A | 11/1991 | Tiffany |

(Continued)

FOREIGN PATENT DOCUMENTS

DE    29713335 U1    11/1997

(Continued)

*Primary Examiner* — Gary Jackson
*Assistant Examiner* — Lindsey Bachman
(74) *Attorney, Agent, or Firm* — Alan W. Cannon

(57) ABSTRACT

Anastomosis devices, tools and methods of performing angled sutureless anastomosis. Devices provided are adapted to be oriented at an acute angle to a host vessel or organ, thereby orienting a graft to be anastomosed to the host by the same angle. The device maintains the angular orientation as it is compressed to join the graft and host.

57 Claims, 19 Drawing Sheets

U.S. PATENT DOCUMENTS

| | | |
|---|---|---|
| 5,089,006 A | 2/1992 | Stiles |
| 5,104,025 A | 4/1992 | Main et al. |
| 5,119,983 A | 6/1992 | Green et al. |
| 5,129,913 A | 7/1992 | Ruppert |
| 5,156,613 A | 10/1992 | Sawyer |
| 5,156,619 A | 10/1992 | Ehrenfeld |
| 5,171,262 A | 12/1992 | MacGregor |
| 5,178,634 A | 1/1993 | Martinez |
| 5,192,289 A | 3/1993 | Jessen |
| 5,193,731 A | 3/1993 | Aranyi |
| 5,205,459 A | 4/1993 | Brinkerhoff et al. |
| 5,211,683 A | 5/1993 | Maginot |
| 5,217,474 A | 6/1993 | Zacca |
| 5,221,281 A | 6/1993 | Klicek |
| 5,222,963 A | 6/1993 | Brinkerhoff et al. |
| 5,234,447 A | 8/1993 | Kaster et al. |
| 5,250,058 A | 10/1993 | Miller et al. |
| 5,250,060 A | 10/1993 | Carbo et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,290,298 A | 3/1994 | Rebuffat et al. |
| 5,292,053 A | 3/1994 | Bilotti et al. |
| 5,304,220 A | 4/1994 | Maginot |
| 5,314,435 A | 5/1994 | Green et al. |
| 5,314,468 A | 5/1994 | Martinez |
| 5,333,773 A | 8/1994 | Main et al. |
| 5,336,233 A | 8/1994 | Chen |
| 5,350,104 A | 9/1994 | Main et al. |
| 5,354,302 A | 10/1994 | Ko |
| 5,364,389 A | 11/1994 | Anderson |
| 5,366,462 A | 11/1994 | Kaster et al. |
| 5,392,979 A | 2/1995 | Green et al. |
| 5,395,030 A | 3/1995 | Kuramoto et al. |
| 5,395,311 A | 3/1995 | Andrews |
| 5,443,497 A | 8/1995 | Venbrux |
| 5,447,514 A | 9/1995 | Gerry et al. |
| 5,454,825 A | 10/1995 | Leeuwen et al. |
| 5,456,712 A | 10/1995 | Maginot |
| 5,456,714 A | 10/1995 | Owen |
| 5,464,449 A | 11/1995 | Ryan et al. |
| 5,465,895 A | 11/1995 | Knodel et al. |
| 5,478,354 A | 12/1995 | Tovey et al. |
| 5,503,635 A | 4/1996 | Sauer et al. |
| 5,515,478 A | 5/1996 | Wang |
| 5,522,834 A | 6/1996 | Fonger et al. |
| 5,524,180 A | 6/1996 | Wang et al. |
| 5,533,661 A | 7/1996 | Main et al. |
| 5,534,761 A | 7/1996 | Crippa |
| 5,540,677 A | 7/1996 | Sinofsky |
| 5,553,198 A | 9/1996 | Wang et al. |
| 5,556,405 A | 9/1996 | Lary |
| 5,558,667 A | 9/1996 | Yarborough |
| 5,571,167 A | 11/1996 | Maginot |
| 5,643,340 A | 7/1997 | Nunokawa |
| 5,645,520 A | 7/1997 | Nakamura |
| 5,657,429 A | 8/1997 | Wang et al. |
| 5,669,918 A | 9/1997 | Balazs et al. |
| 5,669,934 A | 9/1997 | Sawyer |
| 5,676,670 A | 10/1997 | Kim |
| 5,693,088 A | 12/1997 | Lazarus |
| 5,695,504 A | 12/1997 | Gifford et al. |
| 5,702,412 A | 12/1997 | Popov et al. |
| 5,707,362 A | 1/1998 | Yoon |
| 5,707,380 A | 1/1998 | Hinchliffe et al. |
| 5,709,335 A | 1/1998 | Heck |
| 5,709,693 A | 1/1998 | Taylor |
| 5,725,533 A | 3/1998 | Carlsson |
| 5,725,544 A | 3/1998 | Rygaard |
| 5,725,553 A | 3/1998 | Moenning |
| 5,732,872 A | 3/1998 | Bolduc et al. |
| 5,754,741 A | 5/1998 | Wang et al. |
| 5,762,458 A | 6/1998 | Wang et al. |
| 5,779,718 A | 7/1998 | Green et al. |
| 5,789,371 A | 8/1998 | Tracy et al. |
| 5,792,135 A | 8/1998 | Madhani et al. |
| 5,797,900 A | 8/1998 | Madhani et al. |
| 5,797,920 A | 8/1998 | Kim |
| 5,799,661 A | 9/1998 | Boyd et al. |
| 5,799,857 A | 9/1998 | Robertson et al. |
| 5,807,377 A | 9/1998 | Madhani et al. |
| 5,814,073 A | 9/1998 | Bonutti |
| 5,815,640 A | 9/1998 | Wang et al. |
| 5,817,113 A | 10/1998 | Gifford et al. |
| 5,827,316 A | 10/1998 | Young et al. |
| 5,833,698 A * | 11/1998 | Hinchliffe et al. ............ 606/153 |
| 5,841,950 A | 11/1998 | Wang et al. |
| 5,855,583 A | 1/1999 | Wang et al. |
| 5,868,763 A | 2/1999 | Spence et al. |
| 5,875,782 A | 3/1999 | Ferrari et al. |
| 5,878,193 A | 3/1999 | Wang et al. |
| 5,879,371 A | 3/1999 | Gardiner et al. |
| 5,881,943 A | 3/1999 | Heck et al. |
| 5,893,369 A | 4/1999 | LeMole |
| 5,904,697 A | 5/1999 | Gifford et al. |
| 5,907,664 A | 5/1999 | Wang et al. |
| 5,911,036 A | 6/1999 | Wright et al. |
| 5,915,616 A | 6/1999 | Viola et al. |
| 5,921,995 A | 7/1999 | Kleshinski |
| 5,944,730 A | 8/1999 | Nobles et al. |
| 5,947,363 A | 9/1999 | Bolduc et al. |
| 5,957,363 A | 9/1999 | Heck |
| 5,968,089 A | 10/1999 | Krajicek |
| 5,976,159 A | 11/1999 | Bolduc et al. |
| 5,989,276 A | 11/1999 | Houser et al. |
| 6,001,124 A | 12/1999 | Bachinski |
| 6,007,544 A | 12/1999 | Kim |
| 6,013,190 A | 1/2000 | Berg et al. |
| 6,015,416 A | 1/2000 | Stefanchik et al. |
| 6,022,367 A | 2/2000 | Sherts |
| 6,024,748 A | 2/2000 | Manzo et al. |
| 6,030,370 A | 2/2000 | Kupka et al. |
| 6,030,392 A | 2/2000 | Dakov |
| 6,030,395 A | 2/2000 | Nash et al. |
| 6,036,699 A | 3/2000 | Andreas et al. |
| 6,036,700 A | 3/2000 | Stefanchik et al. |
| 6,036,702 A | 3/2000 | Bachinski et al. |
| 6,036,703 A | 3/2000 | Evans et al. |
| 6,036,704 A | 3/2000 | Yoon |
| 6,050,472 A | 4/2000 | Shibata |
| 6,053,390 A | 4/2000 | Green et al. |
| 6,066,144 A | 5/2000 | Wolf et al. |
| 6,066,148 A | 5/2000 | Rygaard |
| 6,068,637 A | 5/2000 | Popov et al. |
| 6,074,401 A | 6/2000 | Gardiner et al. |
| 6,074,416 A | 6/2000 | Berg et al. |
| 6,080,173 A | 6/2000 | Williamson et al. |
| 6,110,187 A | 8/2000 | Donlon |
| 6,110,188 A | 8/2000 | Narciso, Jr. |
| 6,113,612 A | 9/2000 | Swanson et al. |
| 6,117,148 A | 9/2000 | Ravo et al. |
| 6,146,393 A | 11/2000 | Wakabayashi |
| 6,149,658 A | 11/2000 | Gardiner et al. |
| 6,149,681 A | 11/2000 | Houser et al. |
| 6,152,937 A * | 11/2000 | Peterson et al. ............ 606/153 |
| 6,152,945 A | 11/2000 | Bachinski et al. |
| 6,165,185 A | 12/2000 | Shennib et al. |
| 6,167,889 B1 | 1/2001 | Benetti |
| 6,168,623 B1 | 1/2001 | Fogarty et al. |
| 6,171,321 B1 | 1/2001 | Gifford et al. |
| 6,176,413 B1 | 1/2001 | Heck et al. |
| 6,176,864 B1 | 1/2001 | Chapman |
| 6,179,849 B1 | 1/2001 | Yencho et al. |
| 6,186,942 B1 | 2/2001 | Sullivan et al. |
| 6,187,019 B1 | 2/2001 | Stefanchik et al. |
| 6,187,020 B1 | 2/2001 | Zegdi et al. |
| 6,190,396 B1 | 2/2001 | Whitin et al. |
| 6,190,590 B1 | 2/2001 | Randall et al. |
| 6,193,129 B1 | 2/2001 | Bittner et al. |
| 6,193,734 B1 | 2/2001 | Bolduc et al. |
| 6,206,912 B1 | 3/2001 | Goldsteen et al. |
| 6,217,585 B1 | 4/2001 | Houser et al. |
| 6,235,054 B1 | 5/2001 | Berg et al. |
| 6,241,741 B1 | 6/2001 | Duhaylongsod et al. |
| 6,254,617 B1 | 7/2001 | Spence et al. |
| 6,293,955 B1 | 9/2001 | Houser et al. |
| 6,302,905 B1 | 10/2001 | Goldsteen et al. |

| | | |
|---|---|---|
| 6,309,416 B1 | 10/2001 | Swanson et al. |
| 6,361,559 B1 | 3/2002 | Houser et al. |
| 6,371,965 B2 | 4/2002 | Gifford et al. |
| 6,387,105 B1 | 5/2002 | Gifford et al. |
| 6,391,038 B2 | 5/2002 | Vargas et al. |
| 6,398,797 B2 | 6/2002 | Bombard et al. |
| 6,401,721 B1 | 6/2002 | Maginot |
| 6,402,764 B1 | 6/2002 | Hendricksen et al. |
| 6,419,681 B1 | 7/2002 | Vargas et al. |
| 6,428,550 B1 * | 8/2002 | Vargas et al. .............. 606/153 |
| 6,440,163 B1 | 8/2002 | Swanson et al. |
| 6,443,965 B1 | 9/2002 | Gifford et al. |
| 6,451,034 B1 | 9/2002 | Gifford et al. |
| 6,458,140 B2 | 10/2002 | Akin et al. |
| 6,461,320 B1 | 10/2002 | Yencho et al. |
| 6,461,365 B2 | 10/2002 | Bolduc et al. |
| 6,471,713 B1 | 10/2002 | Vargas et al. |
| 6,478,804 B2 | 11/2002 | Vargas et al. |
| 6,491,704 B2 | 12/2002 | Gifford et al. |
| 6,491,705 B2 | 12/2002 | Gifford et al. |
| 6,494,889 B1 | 12/2002 | Fleischman et al. |
| 6,497,710 B2 | 12/2002 | Yencho et al. |
| 6,508,252 B1 | 1/2003 | Berg et al. |
| 6,508,822 B1 | 1/2003 | Peterson et al. |
| 6,511,491 B2 | 1/2003 | Grudem et al. |
| 6,514,196 B1 | 2/2003 | Sullivan et al. |
| 6,514,265 B2 | 2/2003 | Ho et al. |
| 6,517,558 B2 | 2/2003 | Gittings et al. |
| 6,530,932 B1 | 3/2003 | Swayze et al. |
| 6,533,812 B2 | 3/2003 | Swanson et al. |
| 6,537,287 B1 | 3/2003 | Yencho et al. |
| 6,537,288 B2 | 3/2003 | Vargas et al. |
| 6,551,332 B1 | 4/2003 | Nguyen et al. |
| 6,554,764 B1 | 4/2003 | Vargas et al. |
| 6,565,581 B1 | 5/2003 | Spence et al. |
| 6,565,582 B2 | 5/2003 | Gifford et al. |
| 6,573,286 B1 | 6/2003 | Hegde et al. |
| 6,582,463 B1 | 6/2003 | Mowry et al. |
| 6,596,003 B1 | 7/2003 | Realyvasquez et al. |
| 6,599,303 B1 | 7/2003 | Peterson et al. |
| 6,599,313 B1 | 7/2003 | Maginot |
| 6,602,263 B1 * | 8/2003 | Swanson et al. .............. 606/153 |
| 6,605,053 B1 | 8/2003 | Kamm et al. |
| 6,605,098 B2 | 8/2003 | Nobis et al. |
| 6,605,113 B2 | 8/2003 | Wilk |
| 6,607,541 B1 | 8/2003 | Gardiner et al. |
| 6,613,058 B1 | 9/2003 | Goldin |
| 6,613,059 B2 | 9/2003 | Schaller et al. |
| 6,616,675 B1 | 9/2003 | Evard et al. |
| 6,620,176 B1 | 9/2003 | Peterson et al. |
| 6,652,541 B1 | 11/2003 | Vargas et al. |
| 6,666,832 B1 | 12/2003 | Carranza et al. |
| 6,685,739 B2 * | 2/2004 | DiMatteo et al. .............. 623/1.24 |
| 6,695,878 B2 * | 2/2004 | McGuckin et al. .............. 623/1.19 |
| 6,719,769 B2 | 4/2004 | Donohoe et al. |
| 6,972,023 B2 * | 12/2005 | Whayne et al. .............. 606/153 |
| 7,004,949 B2 * | 2/2006 | Yencho et al. .............. 606/142 |
| 7,041,110 B2 * | 5/2006 | Yencho et al. .............. 606/142 |
| 7,063,711 B1 * | 6/2006 | Loshakove et al. .............. 606/153 |
| 7,585,306 B2 * | 9/2009 | Abbott et al. .............. 606/153 |
| 2001/0051809 A1 | 12/2001 | Houser et al. |
| 2002/0013591 A1 | 1/2002 | Fleischman et al. |
| 2002/0032462 A1 | 3/2002 | Houser et al. |
| 2002/0052637 A1 | 5/2002 | Houser et al. |
| 2002/0099393 A1 | 7/2002 | Fleischman et al. |
| 2002/0099394 A1 | 7/2002 | Houser et al. |
| 2002/0173808 A1 | 11/2002 | Houser et al. |
| 2002/0173809 A1 | 11/2002 | Fleischman et al. |
| 2002/0183769 A1 * | 12/2002 | Swanson et al. .............. 606/153 |
| 2003/0023253 A1 | 1/2003 | Vargas et al. |
| 2003/0028205 A1 | 2/2003 | Vargas et al. |
| 2003/0065347 A1 * | 4/2003 | Gifford et al. .............. 606/153 |
| 2003/0074012 A1 | 4/2003 | Nguyen et al. |
| 2003/0078603 A1 | 4/2003 | Schaller et al. |
| 2003/0093118 A1 | 5/2003 | Ho et al. |
| 2003/0120293 A1 | 6/2003 | Yencho et al. |

FOREIGN PATENT DOCUMENTS

| | | |
|---|---|---|
| EP | 0 539 237 A1 | 4/1993 |
| EP | 0517 252 B1 | 8/1995 |
| EP | 0 701800 A1 | 3/1996 |
| EP | 0 913125 A2 | 5/1999 |
| EP | 0 913125 A3 | 5/1999 |
| EP | 0 938870 A1 | 9/1999 |
| EP | 0 820724 B1 | 3/2000 |
| EP | 0 820725 B1 | 3/2000 |
| EP | 0 990420 A2 | 4/2000 |
| EP | 0 885595 B1 | 8/2001 |
| WO | WO 92/08513 | 5/1992 |
| WO | WO 95/17128 | 6/1995 |
| WO | WO 95/35065 | 12/1995 |
| WO | WO 96/25886 | 8/1996 |
| WO | WO 97/25002 | 7/1997 |
| WO | WO 97/27898 | 8/1997 |
| WO | WO 97/31575 | 9/1997 |
| WO | WO 97/47261 | 12/1997 |
| WO | WO 98/02099 | 1/1998 |
| WO | WO 98/07399 | 2/1998 |
| WO | WO 98/19608 | 5/1998 |
| WO | WO 98/19618 | 5/1998 |
| WO | WO 98/19625 | 5/1998 |
| WO | WO 98/19629 | 5/1998 |
| WO | WO 98/19630 | 5/1998 |
| WO | WO 98/19631 | 5/1998 |
| WO | WO 98/19632 | 5/1998 |
| WO | WO 98/19634 | 5/1998 |
| WO | WO 98/19636 | 5/1998 |
| WO | WO 98/30153 | 7/1998 |
| WO | WO 98/37814 | 9/1998 |
| WO | WO 98/40036 | 9/1998 |
| WO | WO 98/42262 | 10/1998 |
| WO | WO 98/47430 | 10/1998 |
| WO | WO 98/55027 | 12/1998 |
| WO | WO 99/08603 | 2/1999 |
| WO | WO 99/17665 | 4/1999 |
| WO | WO 99/18887 | 4/1999 |
| WO | WO 99/21491 | 5/1999 |
| WO | WO 99/37218 | 7/1999 |
| WO | WO 99/38441 | 8/1999 |
| WO | WO 99/38454 | 8/1999 |
| WO | WO 99/40851 | 8/1999 |
| WO | WO 99/40868 | 8/1999 |
| WO | WO 99/45848 | 9/1999 |
| WO | WO 99/52481 | 10/1999 |
| WO | WO 99/62406 | 12/1999 |
| WO | WO 99/62409 | 12/1999 |
| WO | WO 99/62415 | 12/1999 |
| WO | WO 99/63910 | 12/1999 |
| WO | WO 99/65409 | 12/1999 |
| WO | WO 00/09040 | 2/2000 |
| WO | WO 00/10486 | 3/2000 |
| WO | WO 00/12013 | 3/2000 |
| WO | WO 00/15144 | 3/2000 |
| WO | WO 00/15146 | 3/2000 |
| WO | WO 00/15147 | 3/2000 |
| WO | WO 00/15148 | 3/2000 |
| WO | WO 00/15149 | 3/2000 |
| WO | WO 00/27310 | 5/2000 |
| WO | WO 00/27311 | 5/2000 |
| WO | WO 00/27312 | 5/2000 |
| WO | WO 00/27313 | 5/2000 |
| WO | WO 00/33745 | 6/2000 |
| WO | WO 00/41633 | 7/2000 |
| WO | WO 00/53104 | 9/2000 |
| WO | WO 00/56223 | 9/2000 |
| WO | WO 00/56226 | 9/2000 |
| WO | WO 00/56227 | 9/2000 |
| WO | WO 00/56228 | 9/2000 |
| WO | WO 00/59380 | 10/2000 |
| WO | WO 00/66007 | 11/2000 |
| WO | WO 00/66009 | 11/2000 |
| WO | WO 00/69343 | 11/2000 |
| WO | WO 00/69346 | 11/2000 |
| WO | WO 00/69349 | 11/2000 |
| WO | WO 00/69364 | 11/2000 |
| WO | WO 00/72764 | 12/2000 |

| | | | | | | |
|---|---|---|---|---|---|---|
| WO | WO 00/74579 | 12/2000 | | WO | WO 01/19257 | 3/2001 |
| WO | WO 00/76405 | 12/2000 | | WO | WO 01/19259 | 3/2001 |
| WO | WO 01/08601 | 2/2001 | | WO | WO 01/19284 | 3/2001 |
| WO | WO 01/12074 | 2/2001 | | WO | WO 01/34037 | 5/2001 |
| WO | WO 01/015607 | 3/2001 | | WO | WO 01/41653 | 6/2001 |
| WO | WO 01/17440 | 3/2001 | | | | |

* cited by examiner

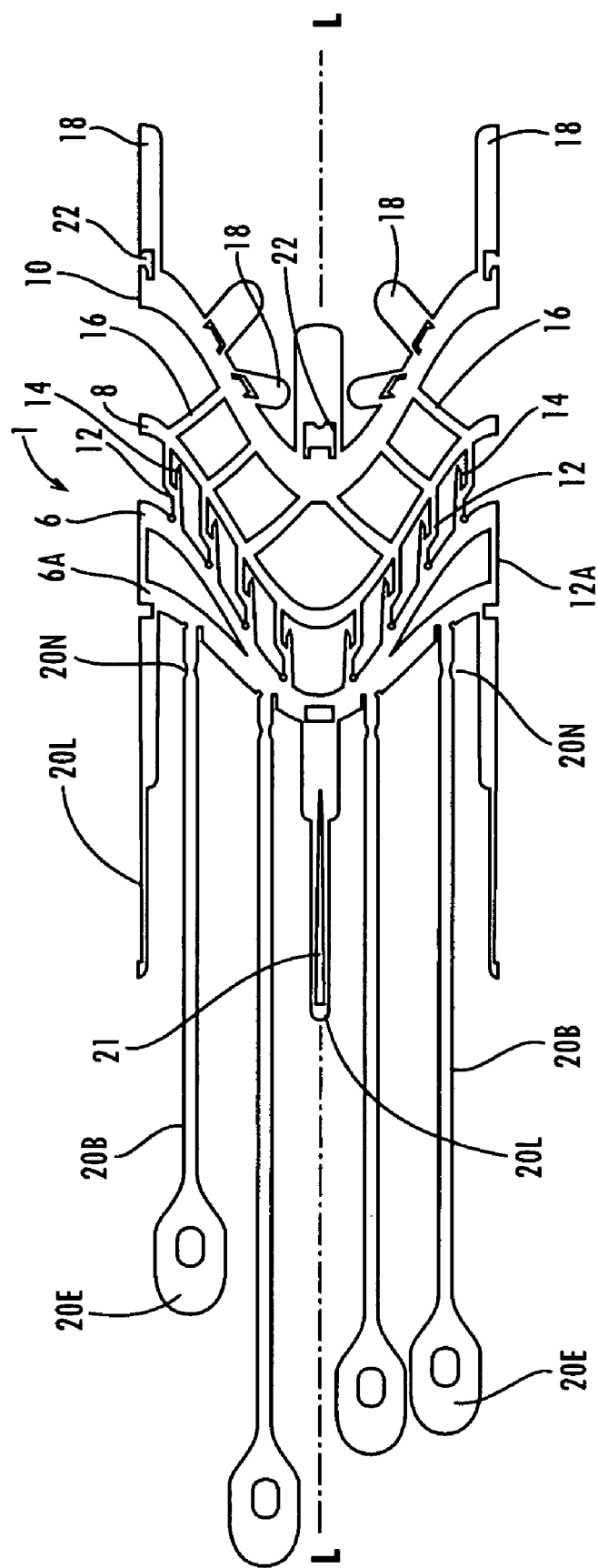

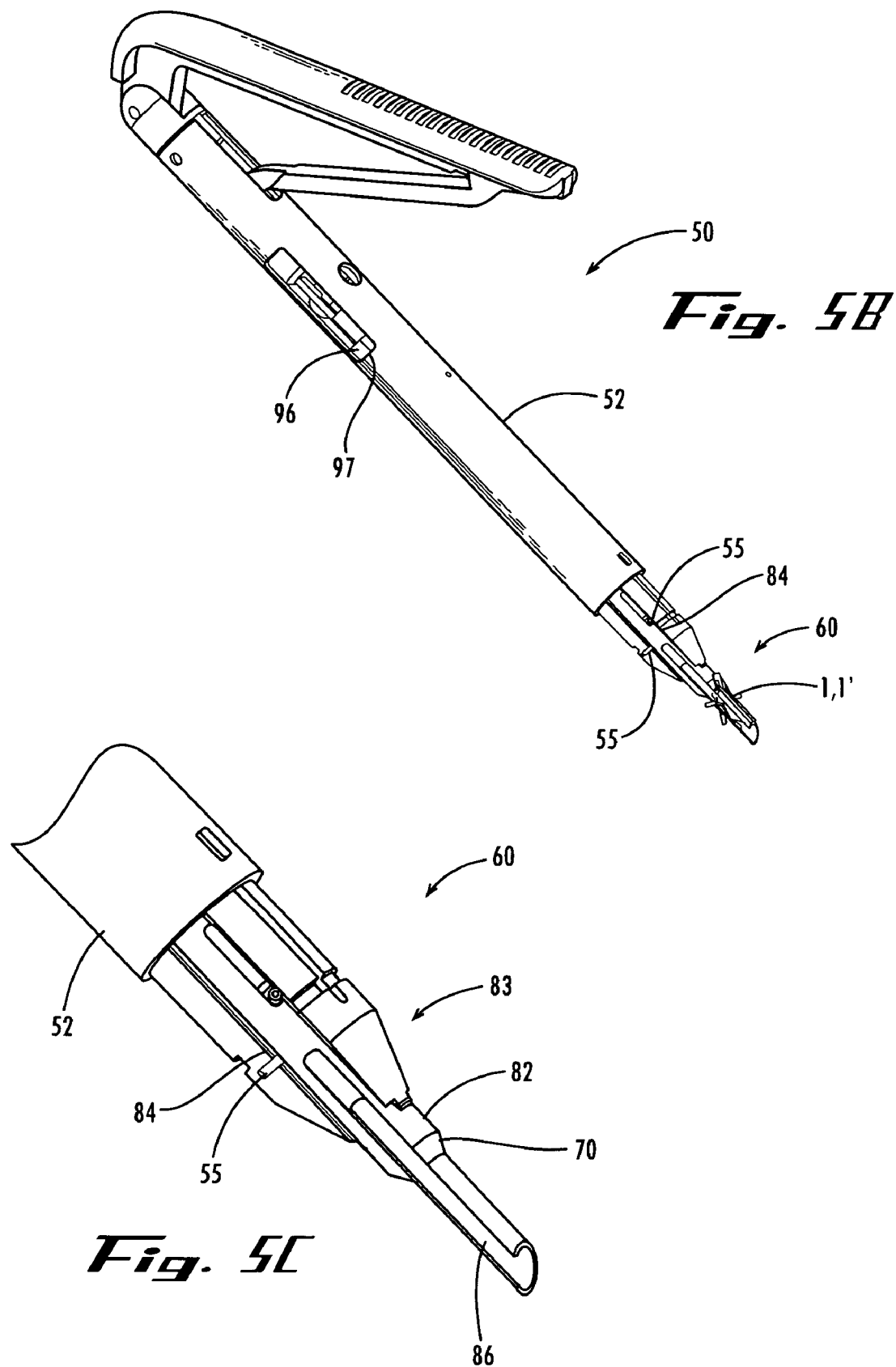

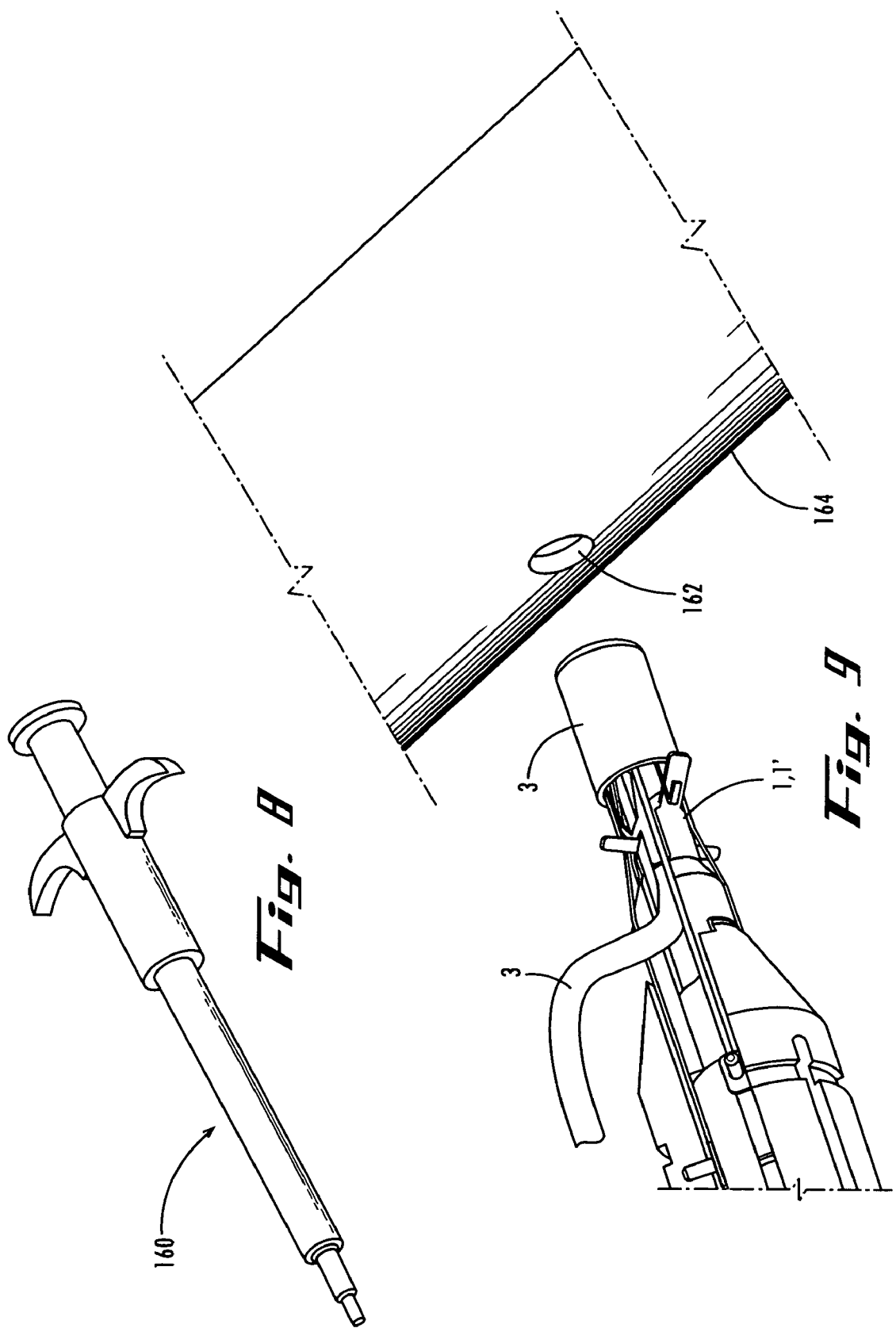

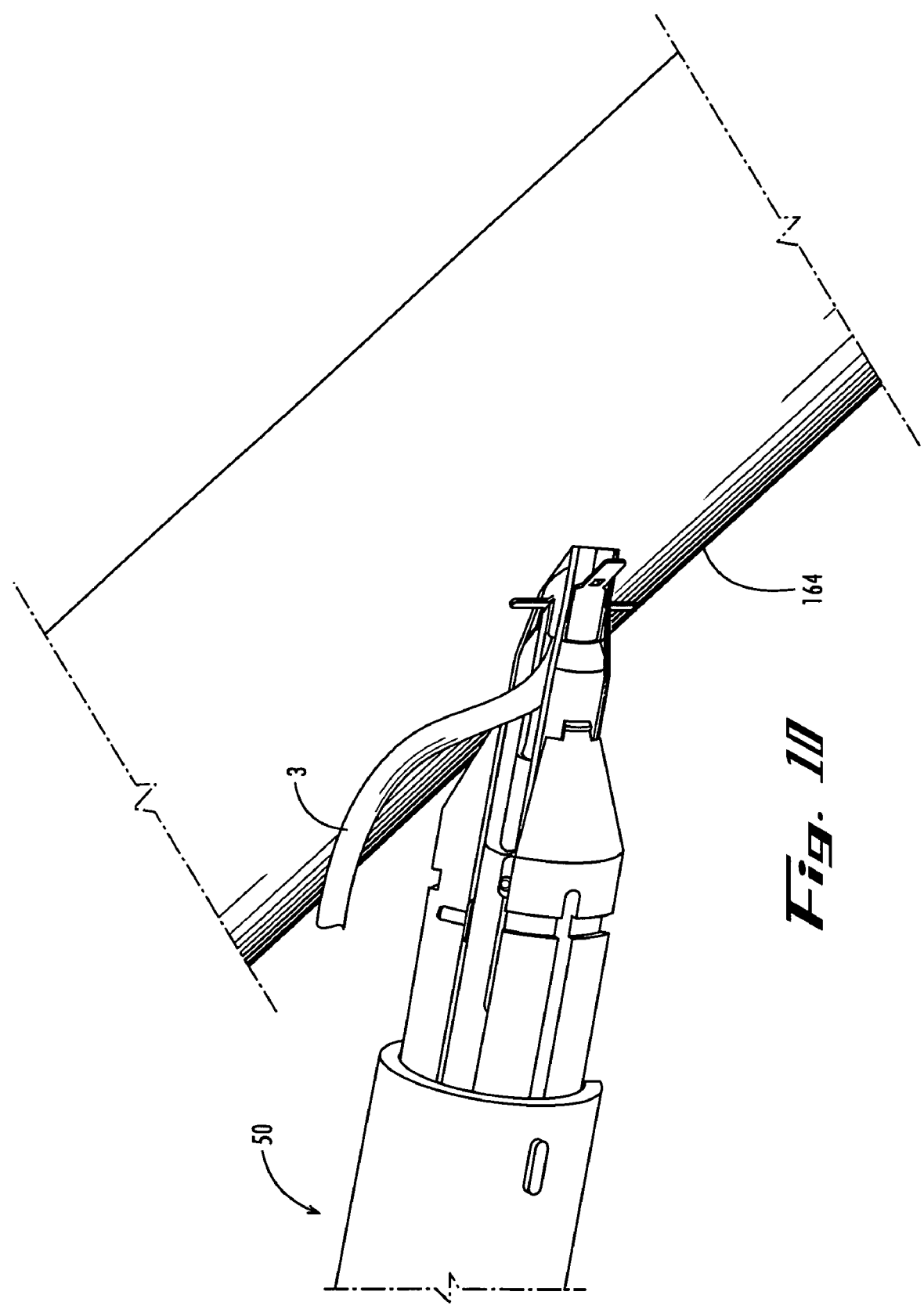

ANGLED ANASTOMOSIS DEVICE, TOOLS AND METHOD OF USING

FIELD OF THE INVENTION

The present invention relates to the field of surgery. More particularly, the present invention relates to devices, tools and methods for performing sutureless anastomoses.

BACKGROUND OF THE INVENTION

There are many medical procedures which require the performance of one or more anastomoses in which a conduit such as a vessel, duct, graft or other tubular structure must be joined to another vessel, duct, or other hollow structure such as an organ to establish continuity between these structures. One of the more prevalent needs for improving anastomosis techniques lies with the treatment of coronary artery disease, where a stenosis of one or more coronary arteries prevents or seriously interferes with a normal blood supply to the heart tissue. In such situations, a total or partial blockage of a coronary artery is often treated by bypassing the obstruction in a heart bypass procedure, such as a coronary artery bypass graft (CABG) procedure, in which a graft is fluidly connected to the blood supply on opposite sides of the site of the stenosis to provide an alternate route for the blood to take on route to the heart.

The graft may be natural conduit, artificial conduit, or a combination of natural and artificial conduits. Typically, a natural conduit in the form of an autograft is used, wherein a saphenous vein is harvested from the leg of the patient or the internal mammary artery is rerouted to be anastomosed downstream of the site of the stenosis.

Conventional CABG procedures are currently performed while the beating of the heart has been stopped, with the circulation and oxygenation of the patient's blood being performed by a heart and lung bypass machine. This procedure requires significant manipulation and clamping of the aorta of the patient. Recently, it has been found that this procedure tends to increase the risk of dislodging plaque that may have accumulated on the internal wall of the aorta in the vicinity of the clamping. Dislodgment of plaque can cause emboli in various locations in the patient's body, cutting off the blood supply downstream of the locus of the embolus, which can cause a stroke or other serious medical complications. Further, the heart-lung bypass machine is thought to cause mechanical damage to the blood cells which furthers the risk of medical complications, due to potential clot formation.

Recently there has been an increase in the performance of beating heart CABG procedures, in which the bypass of one or more stenoses is performed while the patient's heart continues to beat, with the circulation and oxygenation of the patient's blood being performed naturally by the heart and lungs of the patient. While beating heart procedures reduce the associated risks of stroke and other post-operative complications associated with the clamping and manipulation of the aorta and the use of the heart-lung bypass machine, they also increase the difficulty somewhat in performing what were already difficult and delicate anastomosis procedures that must be performed to connect the bypass graft or grafts during the CABG procedure.

The most conventional techniques for making anastomoses involve manually suturing the two tubular conduits together (e.g., manually suturing the graft to the target vessel) around an opening between them. Manual suturing is difficult, time-consuming and requires a great deal of skill and manual dexterity on the part of the surgeon performing the anastomosis. The difficulties in performing anastomoses by manual suturing are magnified when they are done during a beating heart CABG procedure as the beating of the heart introduces perturbations that make it even more difficult to suture in a reliable, consistent and effective manner. These difficulties have largely limited CABG procedures to open surgical settings which provide sufficient surgical access and visualization to complete the delicate anastomoses.

Attempts at performing sutureless anastomoses have, to date, been fraught with problems. Various arrangements for stapling a graft to a host vessel have been proposed, as well as multi-piece compression mechanisms that aim to clamp a graft to a vessel. Some techniques have attempted to perform the procedure intravascularly, through the use of catheter-based delivery of devices and/or grafts. Other approaches have used a unitary connector which is placed partially within the lumen of a graft, and the exposed end is passed through an arteriotomy in a host vessel, and then expanded to lock the graft and host together. All of these approaches have experienced complications such as leakage at the site of the anastomosis, difficulty in the performance of the anastomosis using the techniques required for the particular technology employed, or closure of the graft much sooner than the expected lifetime of performance of the same. For end-to-side anastomoses performed which leave some amount of metal from the anastomosis device exposed to the blood flowing through the host and graft, closure problems have presented, which may be due to blood clotting in response to the exposed metal. Additionally, end-to-side anastomoses that are formed at substantially a right angle may cause turbulence in the required abrupt change in directionality that the blood must take as it flows from the host to the graft, which has been proposed as another cause of clotting/closure or possibly early stenosis. Another problem with an end-to-side anastomosis that substantially forms a right angle or approximates such an angle is the increased risk of kinking of the graft vessel that it causes.

Thus, there is a need for sutureless anastomosis devices, tools and techniques that offer a reliable alternative to suturing techniques and known sutureless techniques, and which are relatively easier to implement while giving consistent, results. It would further be desirable to provide such devices, tool and techniques that would facilitate the performance of higher quality anastomoses than those currently made and with less time required to make the anastomoses.

With continued interest and development toward CABG procedures which are even less invasive than the current techniques for beating heart CABG procedures, it will further be desirable to provide anastomosis techniques which can be performed endoscopically, with the surgeon working outside of the patient.

SUMMARY OF THE INVENTION

Devices, tools and methods for making an angled anastomosis between tubular fluid conduits in the body of a patient are described. An example of a device described includes a unitary structure having a main body disposed annularly about a longitudinal axis and having first and second end portions angled with respect to a normal to the longitudinal axis; a plurality of members extending radially outwardly from the first end portion; and the second end portion having a plurality of spaced struts adapted to buckle in a radially outward direction upon axial compression of the device.

At least one of the struts may be provided with strut portions of unequal length so that, upon buckling, the strut orients at an angle to a normal to the longitudinal axis of the main body.

At least one of the struts may be provided with strut portions of unequal length so that, upon buckling, the strut orients at an angle in a first direction to a normal to the longitudinal axis of the main body, while at least another strut may be provided with strut portions of unequal length so that, upon buckling, it orients at an angle, in a second direction opposite to the first direction, to a normal to the longitudinal axis. At least one other strut may be provided with equal length strut portions so that, upon buckling, this strut orients in a direction normal to the longitudinal axis of the main body.

The device may further include a second set of spaced struts which are collapsible secondarily to the first set of struts, and over a variable range of distance to accommodate for varying wall thicknesses of the tubular conduits being joined by anastomosis.

The end of the second end portion of the device may maintain substantially the same angulation with respect to the normal after buckling of the spaced struts during deployment of the device. Likewise, the end of the first portion maintains substantially the same angulation, thereby maintaining the intended angular orientation of the graft with respect to the host at the site of the anastomosis.

When a second set of struts are employed, the second set of struts begins collapsing after the struts of the second end portion have buckled. The buckled struts prevent the device from passing back out of the opening in the host through which the device and graft have been inserted, further evert the end of the graft, and draw the everted graft against the intimal lining of the host, providing an intima to intima junction with no intervening metal The bending or collapsing of the second set of struts adjusts the device to the particular thicknesses of the host and graft walls, while ensuring a predetermined force is applied to maintain the host and graft in anastomosis.

The first end portion may include a first ring member angled with respect to the normal, with a plurality of members extending radially outwardly from the first ring member. The second end portion may include a second ring member angled with respect to the normal, with the plurality of spaced struts extending from the second ring member toward the first ring member.

A third ring member may be provided in the device, intermediate of the first and second ring members and angled with respect to the normal, in which case the plurality of spaced struts extend from the second ring member to the third ring member; and the second set of spaced struts extend from the first ring member to the third ring member.

All rings may be angled to the normal at substantially the same angle. Optionally, an additional ring portion or member may be provided on the second ring to vary the initial degree of angulation of the second end of the device, to minimize puckering of the graft when everted thereover. The additional ring portion or member may be collapsed against the second ring, during the compression phase, to substantially align the angulation of the second end with that of the first end. Alternatively, the additional ring portion or member may be left in its original configuration, relative to the second ring member, after compression and completion of the anastomosis.

A plurality of elongated members extend from the second end portion toward the first end portion and are adapted to apply a compressive force to the second end portion to buckle the spaced struts. Each of these elongated members may include a weakened portion, such as a neck portion, adapted to fail under tension before the remainder of the elongated member fails, so that, after completion of the compression operation, the elongated members break away from the device, substantially in their entireties.

Each elongated member comprises a free end portion extending away from the second end portion. The free end portions may be provided with an engagement portion or member adapted for engagement with a deployment device, for application of tension to the elongated members by the deployment device.

A plurality of graft tines may be provided to extend out from the second end portion, for engaging or grasping an everted end of a graft as the graft is loaded through the device and everted over the second end portion.

A plurality of spaced locking tines integral with the second end portion and slidably connecting with the first end portion, are provided for locking the relative positions of the first and second end portions upon completion of the anastomosis.

A deployment instrument configured to capture an anastomosis device according to the present invention, and adapted for making an angled anastomosis between tubular fluid conduits in the body of a patient is provided. The instrument includes a tube having an outside diameter dimensioned to receive the anastomosis device there over. The tube further includes a longitudinal slot aligned with a longitudinal axis of the tube, and configured to allow the first conduit to pass therethrough. A stop member is provided, against which the anastomosis device abuts when mounted over the tube. The stop member has an outside diameter greater than the outside diameter of the tube, and may have a distal end angled with respect to a normal to the longitudinal axis of the tube to substantially conform to an angled proximal end of the anastomosis device. Tension actuators adapted to engage members of the anastomosis device are provided. The tension actuators are actuatable in a direction proximal of the tube to apply tension to the members of the anastomosis device.

The members of the anastomosis device, in response to application of tension thereto by the tension actuators, transfer the applied tension to a distal end portion of the anastomosis device, driving the device in compression against the stop member. The stop member and tension actuators are configured to capture the device when mounted on the tube.

The device is further adapted to buckle the device, upon application of tension to the members via the tension actuators.

A locking driver is further provided, which is axially slidable with respect to the stop member and configured to abut locking tines of the anastomosis device. The locking driver may include a distal end angled with respect to a normal to the longitudinal axis of the tube.

A method of performing an angled anastomosis to join a first conduit to a second conduit, is provided, including: inserting a free end of the first conduit through an annular space defined by an anastomosis device comprising a unitary structure having a main body disposed annularly about a longitudinal axis and having first and second end portions, the first and second end portions having end surfaces angled with respect to a normal to the longitudinal axis; and at least one first end member extending further radially outward than a radial extent of the annularly disposed main body; the graft being inserted in a direction from the first end portion to the second end portion so that the free end extends from the angled second end of the device; everting the extending free end of the graft over the angled second end of the device; forming an opening through a wall of the second conduit, wherein the opening is dimensioned to allow the everted end and main body, but not the at least one first end member to pass therethrough; inserting the device and graft into the opening until the at least one first end member abuts the external wall of the second conduit; tilting the device and graft at an angle to the second conduit, wherein the angle to the second conduit is substantially the same as the angle of the first end of the device with respect to the normal to the longitudinal axis; and compressing the device to buckle the second end portion, wherein the second end portion, upon buckling is no longer capable of passing back through the opening.

The compression step is performed only up until a predefined compression force has been reached. The compression step further may at least partially collapse the first end portion after buckling the second end portion.

The compression may compress a portion of the second end before generally compressing the second end portion, wherein the compression of the portion of the second end reorients the degree of angulation of the second end with respect to the normal to the longitudinal axis.

The method may further include locking the relative positions of the first and second end portions after completion of the compression.

As another example, a method of performing an angled anastomosis described includes the steps of: providing the first conduit having been passed through an interior of an anastomosis device and a free end of the first conduit having been everted over at least a portion of the anastomosis device; inserting the anastomosis device and everted free end of the first conduit into an opening in the second conduit and orienting the first conduit to the second conduit at an angle less than ninety degrees; and compressing the device to buckle an end portion of the device that is internal to the second conduit, wherein upon buckling the end portion, the buckled end portion is no longer capable of passing back through the opening in the second conduit.

A second end portion, opposite of the buckled end portion, comprises at least one radially extending member that abuts an external portion of the second conduit and is incapable of passing through the opening in the second conduit.

The compressing step is performed so that a pre-defined compression force limit between the buckled portion and the at least one radially extending member is not exceeded.

The step of compressing may further at least partially collapse the second end portion after buckling the internal end portion.

The compression step forces intima-to-intima contact between the first and second conduits.

The method may further include locking the relative positions of the internal and second end portions after completion of the compressing step.

Further details, features and advantages of the present invention will become apparent to those persons skilled in the art upon reading the details of the devices, tools and methods as more fully described below.

BRIEF DESCRIPTION OF THE DRAWINGS

FIG. 1A shows a flat pattern of an anastomosis device, according to the present invention.

FIG. 5B is a perspective view of another example of a deployment instrument according to the present invention.

FIG. 5C is an enlarged view of a distal end portion of a deployment instrument.

FIG. 8 is a perspective view of an aortotomy punch usable for forming an opening in a target tubular member, for forming an anastomosis at the site of the opening.

FIG. 9 is a partial perspective view showing the opening in the target vessel into which the graft and anastomosis device are to be inserted, and a deployment instrument positioned to insert the graft and anastomosis device.

FIG. 10 is a schematic partial view showing insertion and rotation of a graft and anastomosis device into an opening in a target vessel using a deployment instrument according to the present invention.

DETAILED DESCRIPTION OF THE INVENTION

Figure 1B:
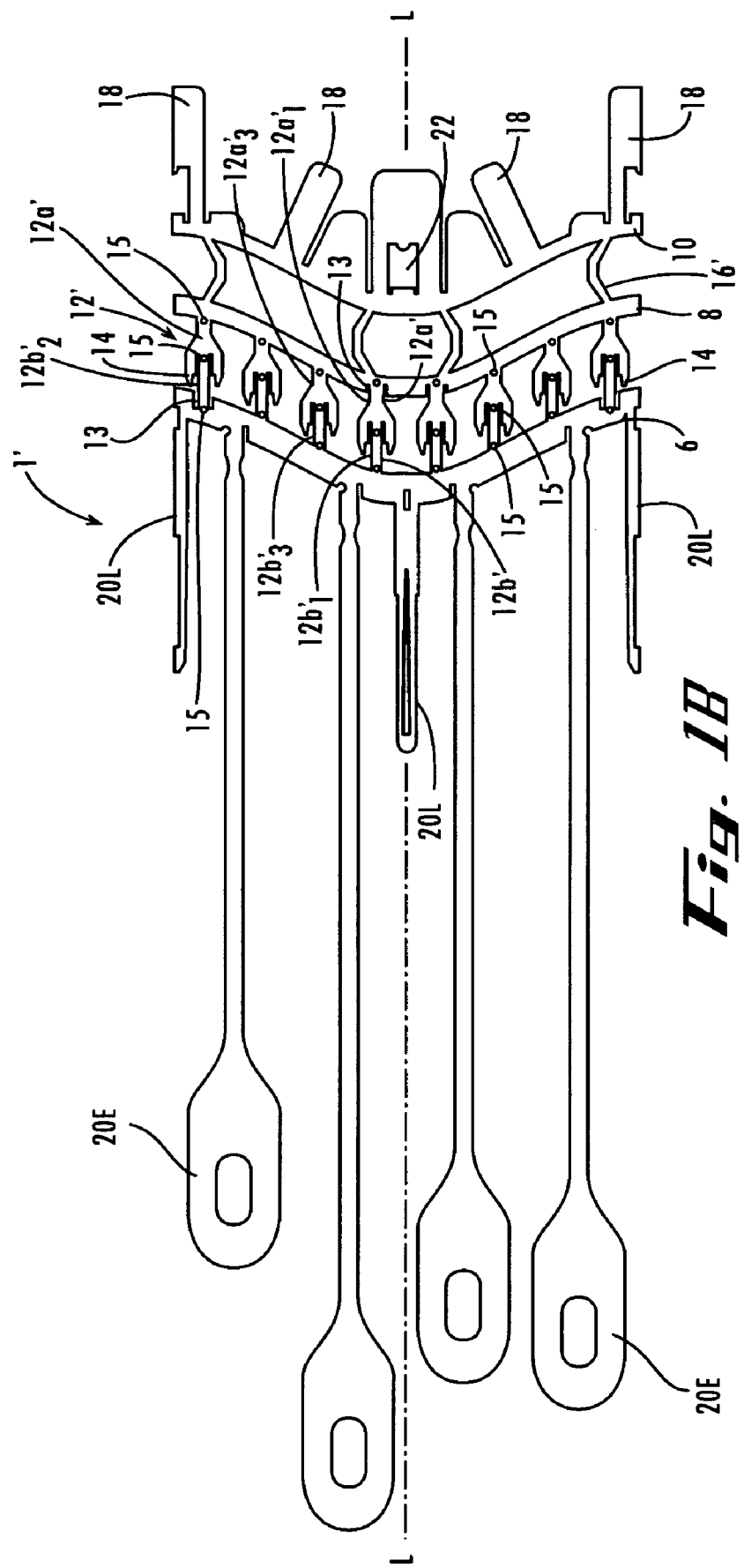
FIG. 1B shows a flat pattern of another example of an anastomosis device, according to the present invention.

Before the present devices, tools and methods are described, it is to be understood that this invention is not limited to a particular device, method step or tool described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a tine" includes a plurality of such tines and reference to "the strut" includes reference to one or more struts and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "tine" is used herein to denote an elongated structure forming a portion of an anastomosis device as described. A "tine" generally has a free end which can have any of a variety of tip configurations, including either a pointed or non-pointed tip.

A "strut" is defined herein to refer to a structurally supporting connecting element which joins at least two other components of an anastomosis device, such as two rings, for example.

A "ring" as used herein, refers to a body-shaping member of the anastomosis device which forms a general configuration of the device used in making an anastomosis.

The present invention provides devices, tools and methods for joining two tubular conduits, such as vessels, organs or other tubular formations, particularly for forming anastomoses in cardiovascular applications, such as those required during the performance of a cardiopulmonary bypass. The present invention avoids the need by prior anastomosis techniques wherein the aorta is clamped to interrupt blood flow to the area of the aortic wall to which a vein is to be anastomosed. Such clamping may result in liberation of plaques and tissue fragments which can lead to organ dysfunction, such as strokes, renal failure, or intestinal ischemia. The anastomosis techniques according to the present invention do not require additional space surrounding the site of the anastomosis and inside the patient to connect the anastomotic device to the target vessel. According to the invention, a sutureless connection can be provided between a graft and a target vessel, while minimizing thrombosis or restenosis associated with the anastomosis. The devices allow the anastomosis to be performed very rapidly, with high reproducibility and reliability, without clamping, and with or without the use of cardiopulmonary bypass.

The anastomosis devices, tools and techniques according to the present invention enable the performance of angled end-to-side anastomoses to thereby improve the blood flow characteristics through the site of the anastomoses and to greatly reduce (if not eliminate) the risk of kinking of the graft at or near the site of the anastomosis. Further, there is no exposure of metal or any part of the anastomosis device to the blood flow through the site of the anastomosis, or to the intima-to-intima contact between the tissues of the host and graft.

Device

FIG. 1A shows, for ease of description, a flat pattern of an anastomosis device 1 according to the present invention. Device 1 includes some of the design characteristics of the anastomosis devices described in our currently pending application Ser. No. 10/746,966 titled "Anastomosis Device, Tools and Method of using, filed on Dec. 24, 2003, and pending application Ser. No. 10/867,430 filed Jun. 14, 2004 titled "Anastomosis Device, Tools and Methods of Using", both of which are incorporated herein, it their entireties, by reference thereto. Practically speaking, device 1 is generally formed integrally, as an annular structure, such as by laser cutting from tubular stock, for example, although it would be possible to cut or stamp a planar structure from a sheet of material and then weld or otherwise fix the device in its annular form. FIG. 1A therefore shows the device 1 as if it were cut along a line parallel to its longitudinal axis L and then flattened into a planar form. The device 1 may be made from stainless steel, such as medical grade 316L stainless steel, for example, or from other plastically deformable materials having appropriate performance characteristics, such as tantalum, tungsten or platinum, for example.

The device 1 can be formed in various sizes to suit the dimensions of a graft or vessel to be joined to another site. For purposes of establishing a proximal anastomosis during performance of a coronary bypass procedure, devices 1 having outside diameters 2 (see FIG. 2) varying within the range of about 3.0 mm to about 7.0 mm, a material thickness of about 0.007"±0.003", and having an initial length 4 of about 0.3" to about 1.0", generally about 0.45", so that they are adapted to accommodate anastomosis of a graft to aortas having wall thicknesses within the range of about 1 mm to about 5 mm.

Figure 2:
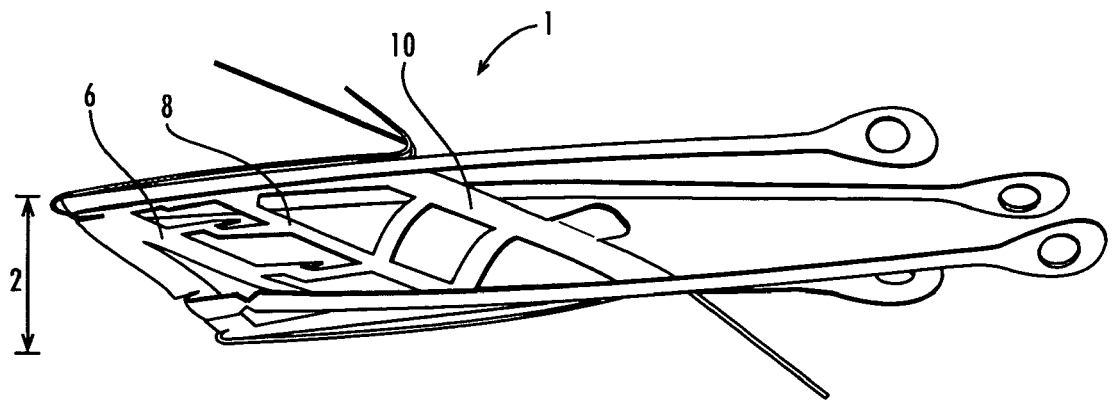
FIG. 2 is a three-dimensional, perspective view of the device shown in FIG. 1A.

Device 1 may include three rings 6, 8 and 10 which form a framework of a cylindrical structure as can be seen in FIG. 2. In order to form a device adapted to angularly join a graft to a host, however, the device 1, when constructed, needs to be "sheared", distorted, or otherwise formed to maintain angular structures to hold the anastomosis in place, both before buckling the device, to align the graft properly, as well as after buckling or otherwise forming the anastomosis, to maintain the graft in its angled configuration with respect to the host at the site of the anastomosis, while at the same time sealing the graft and host by the anastomosis. It can be observed in FIG. 1A that rings 6, 8 and 10 take on a curved or sinusoidal configuration, so that, when configured as a cylindrical, ellipsoidal, oval or otherwise joined, three-dimensional structure (such as shown in FIG. 2, for example), the rings 6, 8 and 10 are oriented at an angle to a normal to the longitudinal axis L of the device 1, wherein the angle of orientation is the same or approximating the angle at which it is desired to orient the graft to the host upon performance of the anastomosis. As shown in FIG. 2, device 1 substantially takes on the shape of an oblique cylinder.

Buckling struts 12 join rings 6 and 8 and are generally equally spaced around the circumferences of the rings 6 and 8 to form a buckling portion of the device 1. Buckling struts 12 may be bent outwardly from an outer surface of an imaginary cylinder defined by rings 6, 8 and 10, to make the buckling portion more susceptible to collapse than the remainder of device 1 upon exertion of compressive forces along the longitudinal axis of device 1. Buckling struts 12 may be further cut out, or formed to have graft tines 14, which may further weaken the buckling struts to make them more susceptible to buckling. Graft tines 14 may be angled to positions extending away from the imaginary cylinder defined by rings 6, 8 and 10 during forming, to position them for anchoring the end of a graft, which function is discussed in greater detail below. Alternatives to graft tines include spikes, glue, a rubber pad that is stegging, or other features designed to hold the graft in an everted configuration during performance of an anastomosis. Another alternative is to completely forego tines or any other structure for holding the graft in the everted configuration, and instead, to simply evert the graft end over the structure of the device 1.

As shown, graft tines 14 formed in buckling struts 12 are formed to have a relatively short length, so as to extend from the general circumference of device 1 by a distance less than the thickness of an everted graft that the graft tines 14 are designed to hold. For example, graft tines 14 are generally formed to have a length less than about 0.25 mm so that it will be impossible to pierce the entire wall of the graft and extend out the everted side of the graft wall. The shorter graft tines 14 cannot extend all the way through the wall of the graft when it is mounted thereon, and, accordingly, the graft tines 14 do not extend from the everted wall of the graft when mounted. In this way, when the device 1 and graft 3 are deployed to form the anastomosis, the metal tines 14 are not exposed in the completed anastomosis, so that no metal is exposed to the intimal surfaces of the anastomosis, or to the blood flowing therethrough. However, it would be possible to form device 1 with longer graft tines that would extend all the way through the wall of the graft vessel, although such an arrangement is currently less preferred.

Support struts 16 join rings 8 and 10 and are generally equally spaced around the circumferences of the rings 8 and 10 to form a supporting portion of the device 1, which buckles or bends only secondarily to the buckling portion. Because of the angulation of rings 8 and 10 with respect to longitudinal axis L, support struts 16 may be formed substantially straight to directly connect rings 8 and 10, as the resulting orientation of such straight struts exposes them to an appropriate bending angle when compressive forces are applied to the device in the direction of the longitudinal axis L. In contrast to buckling struts 12, the bending angle of the support struts 16 is such that support struts 16 maintain substantial conformity with the imaginary cylindrical surface defined by rings 8 and 10. Comparatively, when the buckling section collapses, buckling struts bend outwardly so as to effectively increase the outside diameter of that portion of the device 12, while, in contrast, struts 16 tend to bend or buckle in a direction substantially perpendicular to the direction that struts 12 bend in, so that the struts 16, even after bending, substantially conform to the imaginary cylindrical surface and do not substantially increase the outside diameter of the support portion of the device 1.

External tines 18 extend from ring 10 and are bent substantially perpendicularly to ring 10 from which they extend, during forming. External tines 18 form the contact surface by which device 1 applies pressure to the external surface of a host (e.g., external wall of the aorta) to which a graft held by device 1 is being joined. Locking tines 20L and breakaway tines 20B extend from ring 6 at substantially evenly spaced locations about the circumference of ring 6. Locking tines 20L and breakaway tines 20B have a sufficient length to span the remaining length of device 1 when they are folded over by one hundred and eighty degrees during forming. The external tines 18 which are aligned with locking tines 20L contain locking receptacles 22 through which the respective locking tines 20L pass upon folding them back one hundred and eighty degrees during forming. Due to the skewed orientation of the reminder of the external tines, it has been found that the most convenient locations for the locking receptacles 22 are at the "heel" and "toe" of the resulting ring 10 structure, as these portions maintain the locking receptacles in substantial relative alignment with the longitudinal axis L of the device. The locking tines 20L are bent over to the external side of the general cylindrical shape of device 1, and threaded through the locking receptacles 22 on the external tines which extend radially away from the general cylindrical shape of the device 1, when assembled. By passing locking tines 20 through receptacles 22, locking tines 20 effectively link rings 6 and 10 to provide an important locking feature upon deployment of the device, as will be discussed below. The external tines 18 that contain the locking receptacles 22 may be formed wider than the external tines 18 that do not contain locking receptacles, to compensate for the loss of surface area due to formation of the locking receptacle, as well as to provide a greater surface area against which the respective locking tines 20 are forced.

Breakaway tines 20B include engagement portions 20E adapted for engagement with a deployment device used to deploy device 1 in forming an anastomosis, as will be described in further detail below. As shown, engagement portions are formed as ring structures, each having a central opening through which an engagement portion of the deployment device may be inserted and used to apply a tensile force therethrough. Of course, the present invention is not limited to the ring structure shown, as other engagement features may be substituted, such as hooks, threaded features, or other mechanical coupling expedients as would be readily apparent to one of ordinary skill in the art. Like the locking tines 20L, breakaway tines 20B are bent over to the external side of the general cylindrical shape of device 1, so as to be substantially aligned with the longitudinal axis L, as shown in FIG. 2. By orienting breakaway tines 20B as discussed and shown in FIG. 2, the device 1 is arranged for deployment, where it can be compressed by applying tensile forces through breakaway tines 20B while holding ring 10 relatively fixed in the direction along the longitudinal axis L.

Breakaway tines 20B further include weakened, reduced cross-sectional or "necked" portions 20N which are designed to structurally fail under a significantly less load than that at which the remainder of the breakaway tines fail at. This ensures that the breakaway tines will break away at the locations of the necked portions 20N after device 1 has been deployed, thereby removing substantially all of the extraneous material of the breakaway tines after they have completed their function.

Locking tines 20L may also include weakened sections or cutouts 21 which assist in the preferential bending of the tines in the locations of the weakened sections during the locking phase of deployment of the device. This helps ensure that the locking tines bend into the configuration for which they have been designed, thereby providing the intended secure locking function. Weakened section 21 may be formed by elongated slots, as shown in FIG. 1A, or a series of holes, or other shapes and configurations of cutouts designed to weaken the intended sections of the tines where it is desired to have the bending of the tines begin during the locking phase.

FIG. 1B shows a flat pattern of another anastomosis device 1' according to the present invention. Features of device 1' which are the same as those of device 1 will not be described here to avoid redundancy. Like device 1, device 1' may be formed in various sizes to suit the dimensions of a graft or vessel to be joined to another site, and devices 1' are formed to have outside diameters as described with regard to device 1. Also like device 1, device 1' device 1 substantially takes on the shape of an oblique cylinder when fully constructed, similar to the showing of device 1 in FIG. 2.

Figure 1C:
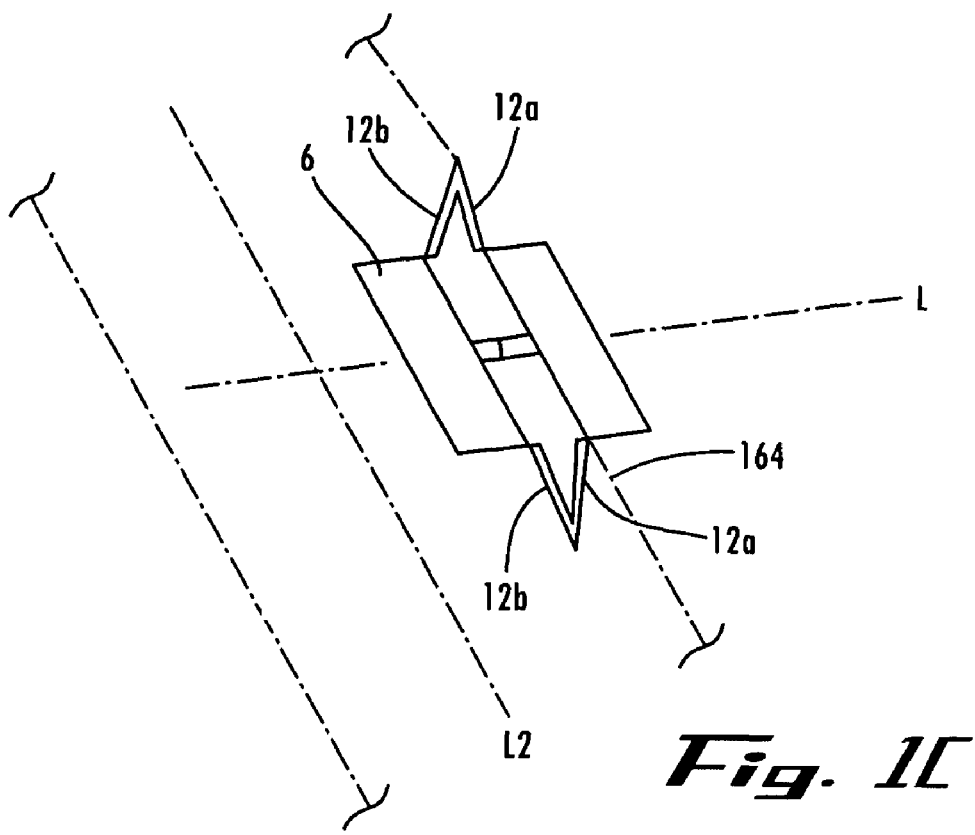
FIG. 1C is a schematic representation showing the orientation of buckled struts having equal strut portion lengths.

Buckling struts 12' join rings 6 and 8 and may be equally spaced around the circumferences of the rings 6 and 8 to form a buckling portion of the device 1'. In this example, the portions 12a' and 12b' are designed to have unequal lengths with regard to some of the bucking struts 12' at predefined locations on device 1. Because device 1,1' is axially compressed along the direction defined by longitudinal axis L during deployment, the buckling struts, as a result of the compression buckle outwardly to a position substantially perpendicular to axis L as a result of the compression, when strut portions 12a and 12b are of equal length, as shown in the schematic representation of FIG. 1C. As can be readily observed in FIG. 1C, those struts 12 which are most nearly aligned with the longitudinal axis L2 of target vessel 164 are those which have the worst approximation to the inner wall of target vessel 164 upon buckling. Those struts 12 which extend normal to longitudinal axis L2, on the other hand, work as intended and abut the inner wall with the intended degree of apposition. The top-most strut (at the top of FIG. 1C) overextends into the wall of vessel 164 and the bottom-most strut (at the bottom of FIG. 1C) does not extend far enough toward the inner wall 164, which may pose a risk of leakage in this area. Those struts which are in between the top-most strut and the struts extending perpendicularly (normal) to axis L2 extend further toward or into the wall of vessel 164 than the struts extending normal to L2, but less than the top-most strut. Those struts which are in between the bottom-most strut and the struts extending perpendicularly (normal) to axis L2 extend less against the wall of vessel 164 than the struts extending normal to L2, but more than the bottom-most strut.

Figure 1D:
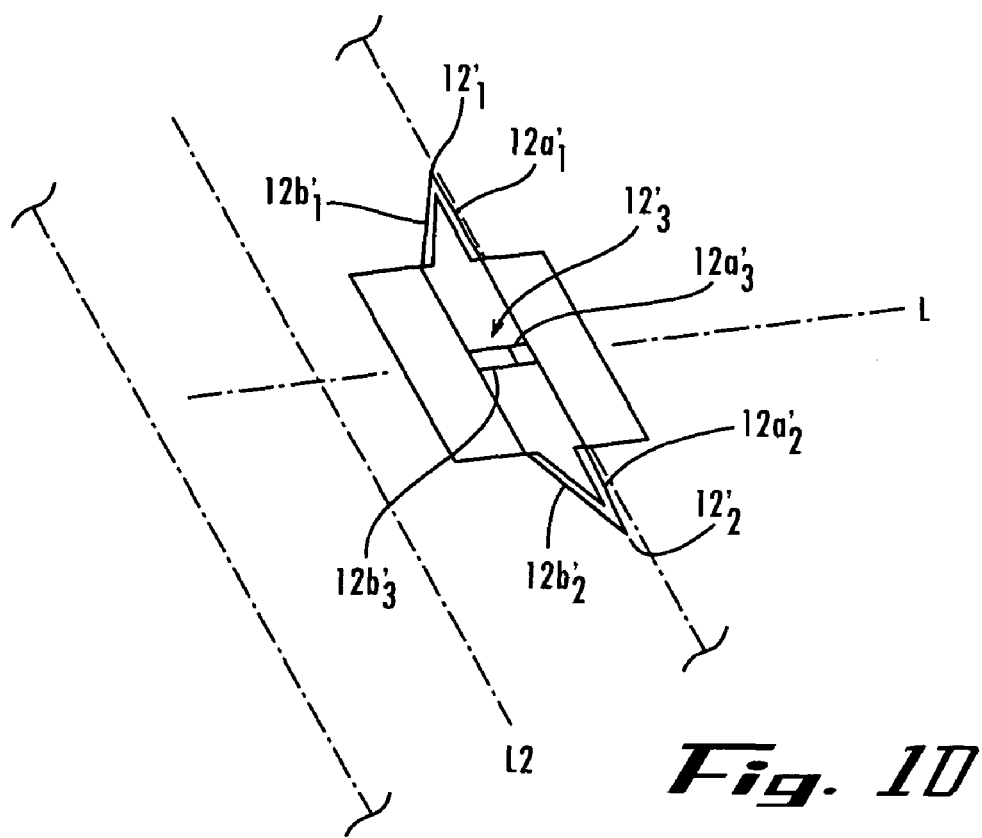
FIG. 1D is a schematic representation showing the orientation of buckled struts wherein some of the buckled struts have unequal strut portion lengths.

In order to have all of the struts buckle into buckled positions which apply substantially equal compression forces against the inner wall of the target vessel 164, the strut portion lengths 12a' and 12b' are varied, depending upon the relative position of each strut 12'. Thus, in the example schematically shown in FIG. 1D, the length of strut portion $12a'_1$ is greater than the length of strut portion $12b'_1$, which causes the buckled strut to angle away from a position normal to axis L, in a direction away from the longer strut portion, $12a'_1$, in this instance. On the other hand, strut portion $12a'_2$ is shorter than strut portion $12b'_2$, which causes strut $12'_2$ to angle from normal in a direction toward the inner wall of vessel 164, which is the direction away from the longer strut portion $12b'_2$. Strut $12'_3$ is oriented normal to axis L2 and therefore strut portions $12a'_3$ and $12b'_3$ may have equal lengths to cause the buckled position of strut $12'_3$ to be substantially normal to axis L.

One technique for making one of the strut portions longer than the other is to cut into one of the rings from which the strut portions extend, such as by forming cuts or slots 15, as shown in FIG. 1B. Alternatively, the center portion of the strut where strut portions 12a' and 12b' may be shifted to make the length of one of strut portions 12a', 12b' longer than the other. Weakened portions 15, such as holes or other cutouts may optionally be formed in predefined areas of the struts in order to ensure that bending occurs in predefined regions of the struts 12'. However, pre-bending or orienting the strut portions slightly outwardly from the cylindrical surface formed by device 1', in the area where portions 12a' and 12b' meet may also, or alternatively serve to ensure that the struts bend in the correct locations during buckling.

Buckling struts 12' may be further cut out, or formed to have graft tines 14, which may further weaken the buckling struts to make them more susceptible to buckling. Graft tines 14 may be angled to positions extending away from the imaginary cylinder defined by rings 6, 8 and 10 during forming, to position them for anchoring the end of a graft, as also noted with regard to FIG. 1A above. Alternatives to graft tines include spikes, glue, a rubber pad that is stegging, or other features designed to hold the graft in an everted configuration during performance of an anastomosis. Another alternative is to completely forego tines or any other structure for holding the graft in the everted configuration, and instead, to simply evert the graft end over the structure of the device 1'.

Support struts 16 join rings 8 and 10 and may be generally equally spaced around the circumferences of the rings 8 and 10 to form a supporting portion of the device 1', which buckles or bends only secondarily to the buckling portion. In the example shown, because the angulation of this device (i.e., angle to be formed between the target vessel and graft vessel) is less acute than that intended by the use of the example shown in FIG. 1A, support struts 16' may be formed "bent" or angulated to predispose their bending or collapse so as to maintain substantial conformity with the imaginary cylindrical surface defined by rings 8 and 10. However, it must be noted here, that either of the examples described in FIGS. 1A and 1B may be formed to have a degree of angulation selected from a large range of available angles, as discussed herein.

FIG. 2 shows device 1 of FIG. 1A in its three dimensional configuration, which may be formed by shaping and welding a flat configuration as described above, but is preferably formed by directly cutting it from tubular stock, such as by laser cutting, for example. Further, device 1 may be electropolished after cutting (e.g., laser cutting), for about one minute, for example.

While the above description has been directed to a device comprising three rings, the present invention may also be applied to a device having two rings interconnected by buckling struts, without the third ring and bending struts, similar to the concept of the two ring device described in application Ser. No. 10/746,966, although the rings and struts are positioned according to the description above to provide a sheared or angled device. Such a device is also actuated by breakaway tines, as described above and includes the other features of the three ring device, such as external tabs and locking tines, but has less capacity to adjust to varying wall thicknesses of hosts and grafts encountered during anastomosis procedures.

Deployment Instrument

Figure 3A:
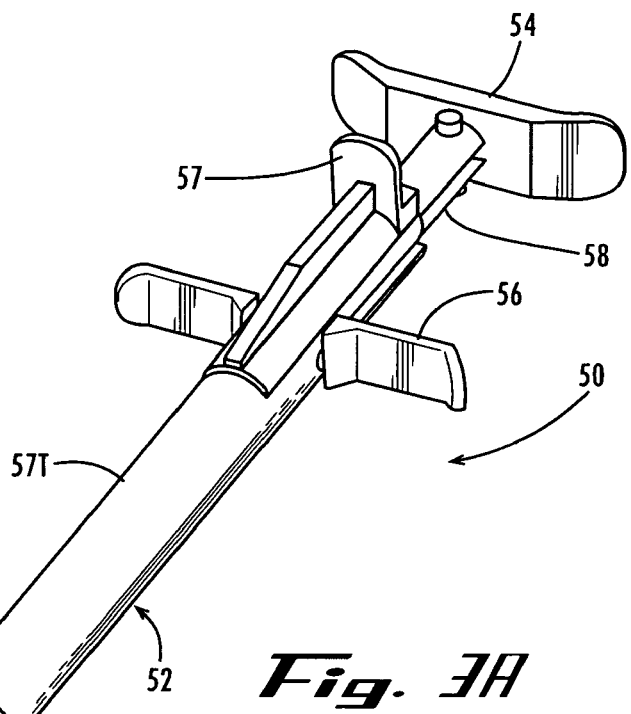
FIG. 3A shows a perspective view of a deployment instrument according to the present invention.

FIG. 3A is a perspective view of an example of a deployment instrument 50, which is configured to receive and deliver an anastomosis device in performance of an angled end-to-side anastomosis according to the present invention. Generally speaking, instrument 50 includes a main body 52, which is configured to be hand held by the operator. A distal tip portion 60 of instrument 50 is configured for receiving, holding and deploying an anastomosis device 1,1' according to the present invention. Tension actuators 55 are fixed to tube 62 and are connected to handle 56 so as to be slidably positionable with respect to main body 52. An elongated member 58 fixes handle 54 with respect to main body 52. Handle 54 is fixed to elongate member 58 and provides leverage to the user during movements of handles 56 and 57, described below.

Figure 3B:
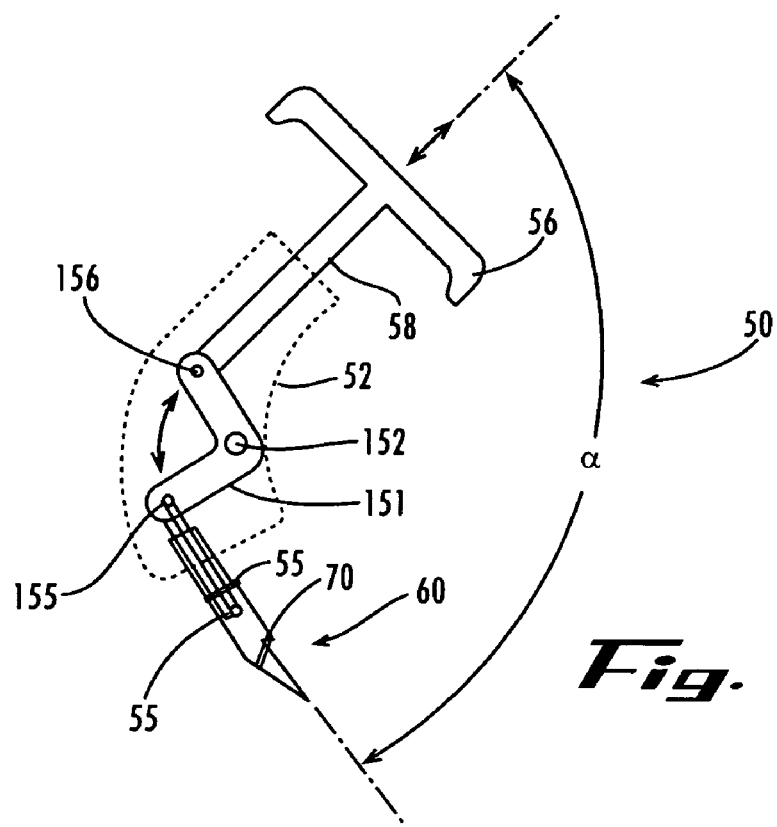
FIG. 3B shows a variation of the instrument shown in FIG. 3A.

The main body 52 may advantageously be made long and slender to separate the distal tip portion 60 from handles 54, 56 and 57 by a sufficient distance to adapt the device to be employed in very small spaces and even endoscopically in some situations. Alternatively, distal tip portion 60 may be formed at an angle to the longitudinal axis of main body 52, to permit tilting of device 50 during deployment of a device 1 which at the same time orients the main body 52 substantially perpendicularly to the surgical site, thereby ensuring maximum working space in the vicinity of handles 54, 56 and 57. FIG. 3B is a schematic representation showing the interconnection between handle 56 with tension actuators 55, to control the sliding motion of tension actuators 55 relative to stop member 70 during buckling/deployment of device 1,1'. Rocker 151 is pivotally mounted with respect to body 51 at pivot mount 152. A shaft extending from handle 56 is pivotally mounted to rocker 151 at pivot mount 156, and tension actuators 55 are connected to rocker 151 via wires, cables or small shafts at pivot mount 155. This mechanism translates the sliding actuation of handle 56 to tension actuators 55. Although not shown in this schematic, a similar mechanism may be employed for actuation of locking driver 68 by handle 57. The handles 54, 56 and 57, main body 52 and elongated member 58 may all be formed of a structurally rigid polymer, such as ABS plastic, polycarbonate or other materials which are sufficiently rigid and biocompatible. Tension actuators 55 and stop member 70, as well as distal tip 60 are generally made of metal, such as stainless steel or other biocompatible, structurally rigid metal.

Figure 4:
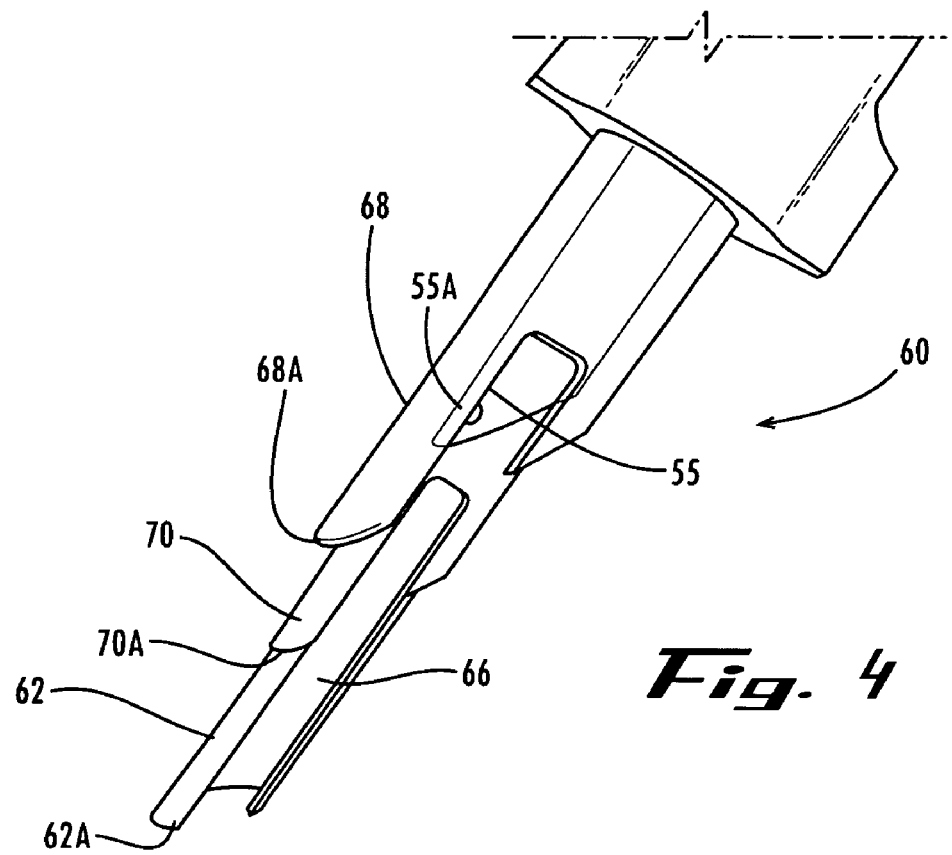
FIG. 4 is an enlarged view of the distal tip portion of the instrument shown in FIG. 3A.

FIG. 4 is an enlarged view of the distal tip portion 60 of instrument 50, which is enlarged from the section delineated by phantom circle 4 in FIG. 3A. Distal tip portion 60 includes a substantially cylindrically shaped tube 62, which is dimensioned for receiving and holding an anastomosis device 1,1' according to the present invention. Of course, those of ordinary skill in the art would recognize that tube 62 could be formed with other conforming cross-sectional shapes, for example, elliptical, oval or other cross-sectional shape tubes could be substituted, while optionally providing a device 1 having an inside perimeter with a conforming shape. The outside diameter of the arrangement is slightly less than the inside diameter of a device 1 for which it is designed to receive and deploy. For example, a clearance of about 0.002" may be provided between the inside diameter of the device 1,1' and the outside diameter of tube 62. Such a design allows the device 1,1' to be freely slid over tube 62 when in the loading configuration, while at the same time not allowing so much clearance as to allow the device 1,1' to become misaligned. Because of this fairly close tolerance requirement, instruments 50 having varying tube 62 outside diameters are manufactured to match the inside diameters of the various device sizes that may be needed. As discussed above, the device sizes may vary in the range of about 3.0 mm to about 7.0 mm inside diameter, which necessitates the provision of a series of delivery instruments 50, or at least distal portions 60, to accommodate the size variations.

Tube 62 is provided with a longitudinal slot so as to define a channel 66 that allows a graft (attached to a device 1,1') to extend externally of instrument 50, and to render the cross-sectional views of the tube 62 to appear somewhat "C-shaped". Advantageously, this feature allows a graft to be side fed into instrument 50 and also does not require that both ends of the graft be free in order to perform an anastomosis according to the invention. Further, tube 62 includes tension actuators 55 (see for example, one end 55A of cross pin 55 shown), such as cross-pins, as shown, to receive and secure engagement portions 20E of breakaway tines 20B. Although only one end 55A of cross-pin 55 is shown in FIG. 4, a pair of pins 55 extend in this example through tube 62 and out the opposite side not shown, so that each of the pins provides two end portions, each of which an engagement portion 20E is looped over upon loading a device 1, 1'. Grooves 84 may be provided in the tube that ends with locking member 68A to each receive part of an engagement portion 20E therein and thus prevent engagement portions 20E of breakaway tines 20B from slipping off or otherwise releasing from tension actuators 55.

Tube 62 may be formed with an angled distal end which is angled with respect to a perpendicular line to the longitudinal axis, and may be angled to substantially conform to the angled orientation of device 1,1'. A stop member, surface or feature 70 may be integrally formed, or bonded, welded or otherwise fixed relative to tube 62. Stop member 70 is preferably formed of metal and has an outside diameter that is greater than the inside diameter of device 1,1' and preferably about equal to the outside diameter of device 1. The distal edge or surface 70a of stop member 70 is angled to correspond to the angled proximal surface of the device (i.e., ring 10) which is mated against the stop member upon loading the device, and against which the device 1,1' is compressed during deployment.

A locking driver (device lock) 68 is provided concentrically over tube 62 and is longitudinally slidable with respect thereto. Locking driver 68 is linked to handle 57 via compression spring 74 which functions as a force limiter during the locking operation, as handle 57 and locking driver are slid with respect to main body 52 as described in more detail below. With this arrangement, locking driver 68 can be advanced toward (or withdrawn away from) the distal end of tube 62 through corresponding movement of handle 57 in the appropriate direction. Movement of handle 57 slides tube 57t in the desired longitudinal direction with respect to tube 62, which it turn moves locking drive via action through spring 74. Locking driver 68 may have a distal end or surface that substantially conforms to the angulation of ring 10 to provide a more even and consistent compression force to ring 10 during deployment of device 1.

Device 1,1', is maintained in alignment with instrument 50 by the capture of breakaway tines 20B by tension actuators 55. This alignment ensures that the proximal end or surfaces of ring 10 will substantially conform to distal stop member surface 70a and that the distal end or surface 68A of device lock 68 will evenly meet the locking members 20L to perform the locking function, as described below. The device 1,1' is slid onto the distal portion 60 until it makes contact with stop member 70. The proximal end 70A of stop member 70 may be beveled to provide a ramping surface against which device 1 comes to rest. In this way, stop member 70 not only helps to correctly position device 1 in a longitudinal position along the distal portion 60, but also performs a centering function to keep device 1 properly centered on the distal portion 60 of deployment device 50.

Once device 1,1' is properly positioned and abutted against stop member 70, locking member 68 is slid proximally (toward handle 54) with respect to tension actuators, causing a compression of spring 74 and exposing the tension actuators for loading the breakaway tines/engagement portions 20E thereon. After positioning the engagement features 20E over tension actuators 55 (as shown, cross pins, although other engagement features such as clamps, mating threads or other known engagement features could be substituted), locking member 68 is released and returns to its starting position as it is biased there by decompression of spring 74, whereby grooves 84 receive the edges of engagement portions 20E to capture the engagement portions 20E and prevent them from coming off cross pins 55, while at the same time capturing device 1,1' to fix its position on device 50. In the capture configuration as described, device 1,1' is securely held by the abutment of ring 10 against stop member 70, and by the tension on breakaway members 20B supplied by tension actuators 55.

Figure 5A:
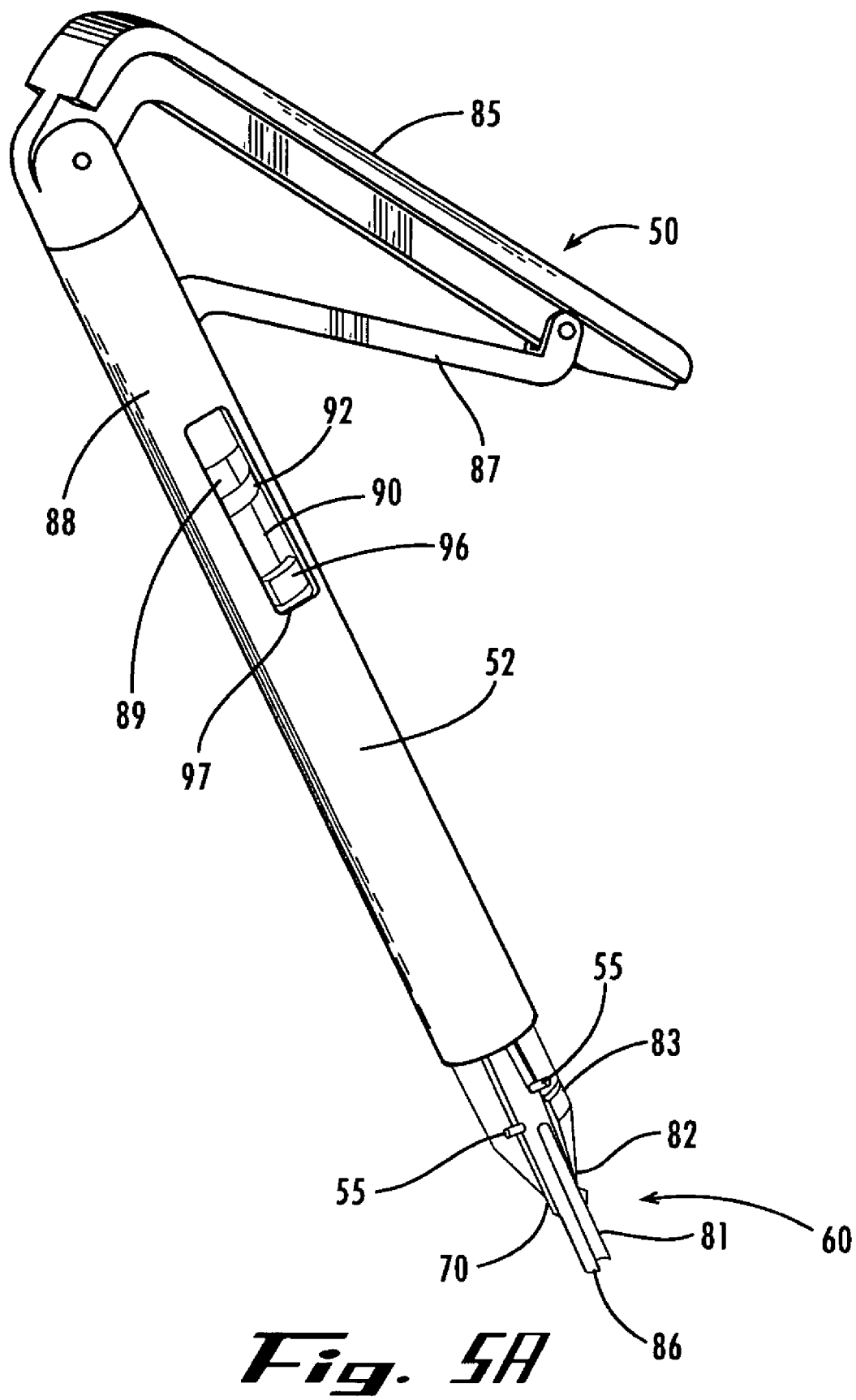
FIG. 5A is a perspective view of another example of a deployment instrument according to the present invention.

FIG. 5A shows a perspective view of another example of a deployment instrument 50, which is configured to receive and deliver an anastomosis device in performance of an angled end-to-side anastomosis according to the present invention. Generally speaking, instrument 50 includes a main body 52, which is configured to be hand held by the operator. A distal tip portion 60 of instrument 50 is configured for receiving, holding and deploying an anastomosis device 1,1' according to the present invention. The end of distal tip portion may be substantially perpendicular to the longitudinal axis of instrument 50, as shown in FIG. 5A, or may be angled or beveled with respect to the longitudinal axis, as shown in FIG. 5B. The main body 52 may advantageously be made long and slender to separate the distal tip portion 60 from handle 85 and linkage 87 by a sufficient distance to adapt the device to be employed in very small spaces and even endoscopically in some situations. Alternatively, distal tip portion 60 may be formed at an angle to the longitudinal axis of main body 52, to permit tilting of device 50 during deployment of a device 1,1' which at the same time orients the main body 52 substantially perpendicularly to the surgical site, thereby ensuring maximum working space in the vicinity of handle 85.

Tension actuators 55, such as cross-pins, as shown, are provided to receive and secure engagement portions 20E of breakaway tines 20B. Although only one end of each cross-pin 55 is shown in FIG. 5A, pins 55 extend through main shaft 81 and out the opposite side not shown, so that each of the pins provides two end portions, each of which an engagement portion 20E is looped over upon loading a device 1, 1'. Grooves 84 may be provided in locking member 83 to each receive part of an engagement portion 20E therein and thus prevent engagement portions 20E of breakaway tines 20B from slipping off or otherwise releasing from tension actuators 55.

The distal end portion of main shaft 81 is dimensioned for receiving and holding an anastomosis device 1,1' according to the present invention (Note that FIG. 5B shows anastomosis device 1,1' mounted on the distal tip portion 60 of instrument 50). Of course, those of ordinary skill in the art would recognize that tube 81 could be formed with other conforming cross-sectional shapes, for example, elliptical, oval or other cross-sectional shape tubes could be substituted, while optionally providing a device 1,1' having an inside perimeter with a conforming shape. The outside diameter of the arrangement is slightly less than the inside diameter of a device 1,1' for which it is designed to receive and deploy. For example, a clearance of about 0.002" may be provided between the inside diameter of the device 1,1' and the outside diameter of tube 81. Such a design allows the device 1,1' to be freely slid over tube 81 when in the loading configuration, while at the same time not allowing so much clearance as to allow the device 1,1' to become misaligned. Because of this fairly close tolerance requirement, instruments 50 having varying tube 81 outside diameters are manufactured to match the inside diameters of the various device sizes that may be needed. As discussed above, the device sizes may vary in the range of about 3.0 mm to about 7.0 mm inside diameter, which necessitates the provision of a series of delivery instruments 50, or at least distal portions 60, to accommodate the size variations.

Tube 81 is provided with a longitudinal slot so as to define a channel 86 that allows a graft (attached to a device 1,1') to extend externally of instrument 50, and to render the cross-sectional views of the tube 81 to appear somewhat "C-shaped", as can be seen best in FIGS. 5A and 5C. Advantageously, this feature allows a graft to be side fed into instrument 50 and also does not require that both ends of the graft be free in order to perform an anastomosis according to the invention. Further, this feature also allows the distal anastomosis of a graft initially having two free ends (such as a saphenous vein graft or a radial artery graft, as two, non-limiting examples) prior to the proximal anastomosis of the graft.

The main body 52 may advantageously be made long and slender to separate the distal tip portion 60 from handle 85 by a sufficient distance to adapt the device to be employed in vary small spaces and even endoscopically in some situations. Alternatively, distal tip portion 60 may be formed at an angle to the longitudinal axis of main body 52, to permit tilting of device 50 during deployment of a device 1 which at the same time orients the main body 52 substantially perpendicularly to the surgical site, thereby ensuring maximum working space in the vicinity of handle 85. Handle 85, linkage 87, locking member 83 and main body 52 may all be formed of a structurally rigid polymer, such as ABS plastic or other materials which are sufficiently rigid and biocompatible. Tension actuators 54, tube 82 including stop member 70 and tube 81 are generally made of metal, such as stainless steel or other biocompatible, structurally rigid metal.

Tube 82 is relatively fixed with respect to main body 52 or integral therewith and includes a beveled or contoured stop member 70 at its distal end. Tube 82 may optionally be formed with an angled distal end (stop member 70) which is angled with respect to a perpendicular line to the longitudinal axis, and may be angled to substantially conform to the angled orientation of device 1,1'. Stop member, surface or feature 70 may be integrally formed, or bonded, welded or otherwise fixed relative to tube 82. Stop member 70 has an outside diameter that is greater than the inside diameter of device 1,1' and preferably about equal to the outside diameter of device 1,1'

Figure 5D:
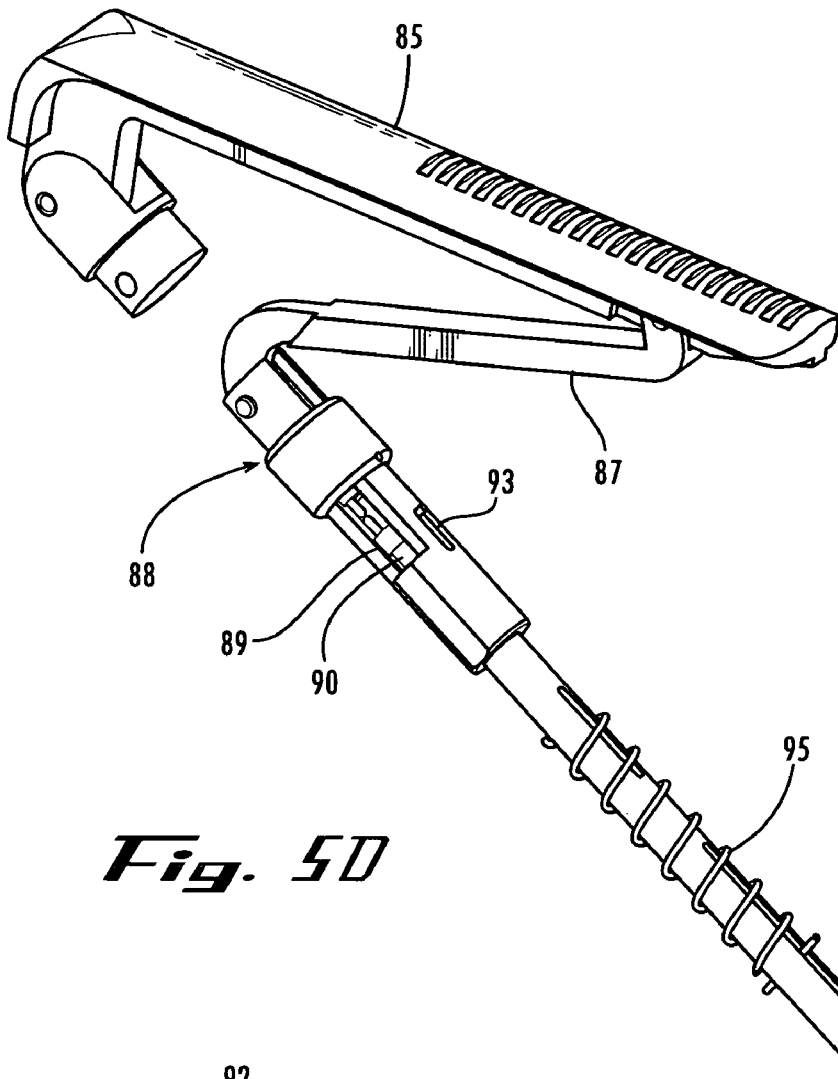
FIG. 5D is a partially exploded view, showing components of the instrument of FIG. 5A or FIG. 5B.

Tube 81 is linked to tension actuator handle 85 via linkage 87, actuation link 88. and clutch member 89, see FIG. 5D. Clutch member 89 is interlinked, such as by cross pins 92 for example, between actuation link 88 and a proximal end of a shaft 90 which integrally extends from tube 81. Actuation link 88 provides a secondary connection to shaft 90 via a slot 93 through which shaft 90 extends but cannot escape from the distal end of actuation link 88.

Figure 5E:
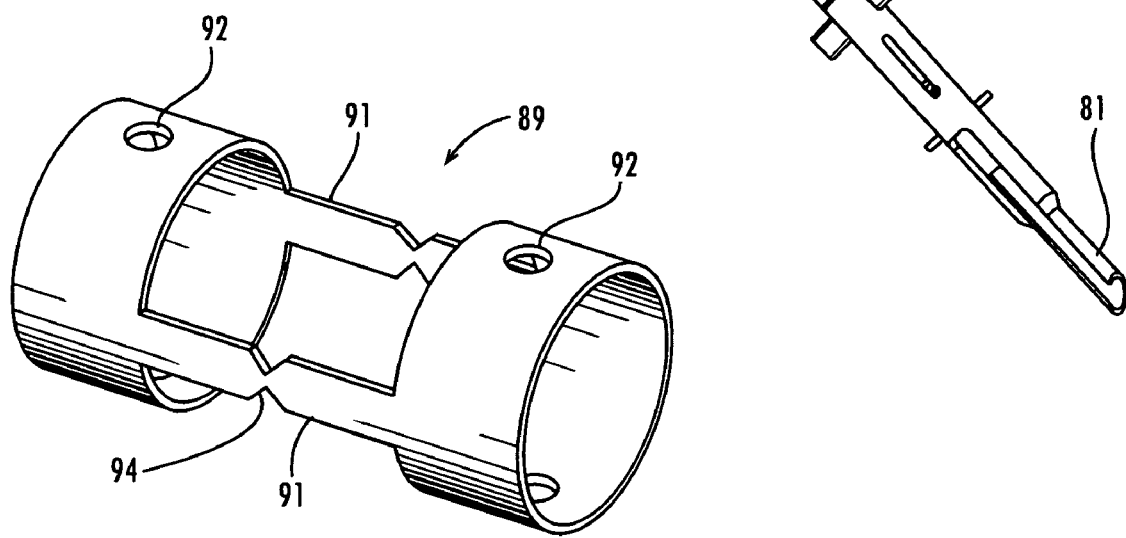
FIG. 5E is a perspective view of a clutch member that may be employed in the instruments shown in FIGS. 5A and 5B.

FIG. 5E is a perspective view of an example of a clutch member 89 that may be used in the instrument of FIG. 5A or FIG. 5B. Clutch member 89 includes a reduced section of material 91 which further necks down 94 or reduces to form a preferential location for failure of the member 89 under tension. The necked down region 94 is designed to have a predetermined load failure under a predetermined amount of tension. For example, failure may be designed to occur at about twelve±1 pounds of tension.

Locking driver (locking member) 83 is provided concentrically over tube 82 and is longitudinally slidable with respect thereto. Locking member 83 is biased toward the locking position wherein locking member drives locking tines 20L into the locked configuration, but is shown in loaded position in FIG. 5A. Locking member is further retractable to present tension actuators 55 for installing the breakaway tine engagement portions 20E thereover as has been described. After installation of the breakaway tine engagement portions 20E, release of the locking member 83 allows it to be repositioned, under the biasing force of biasing member 95 to the loaded position shown in FIGS. 5A-5B.

Figure 5F:
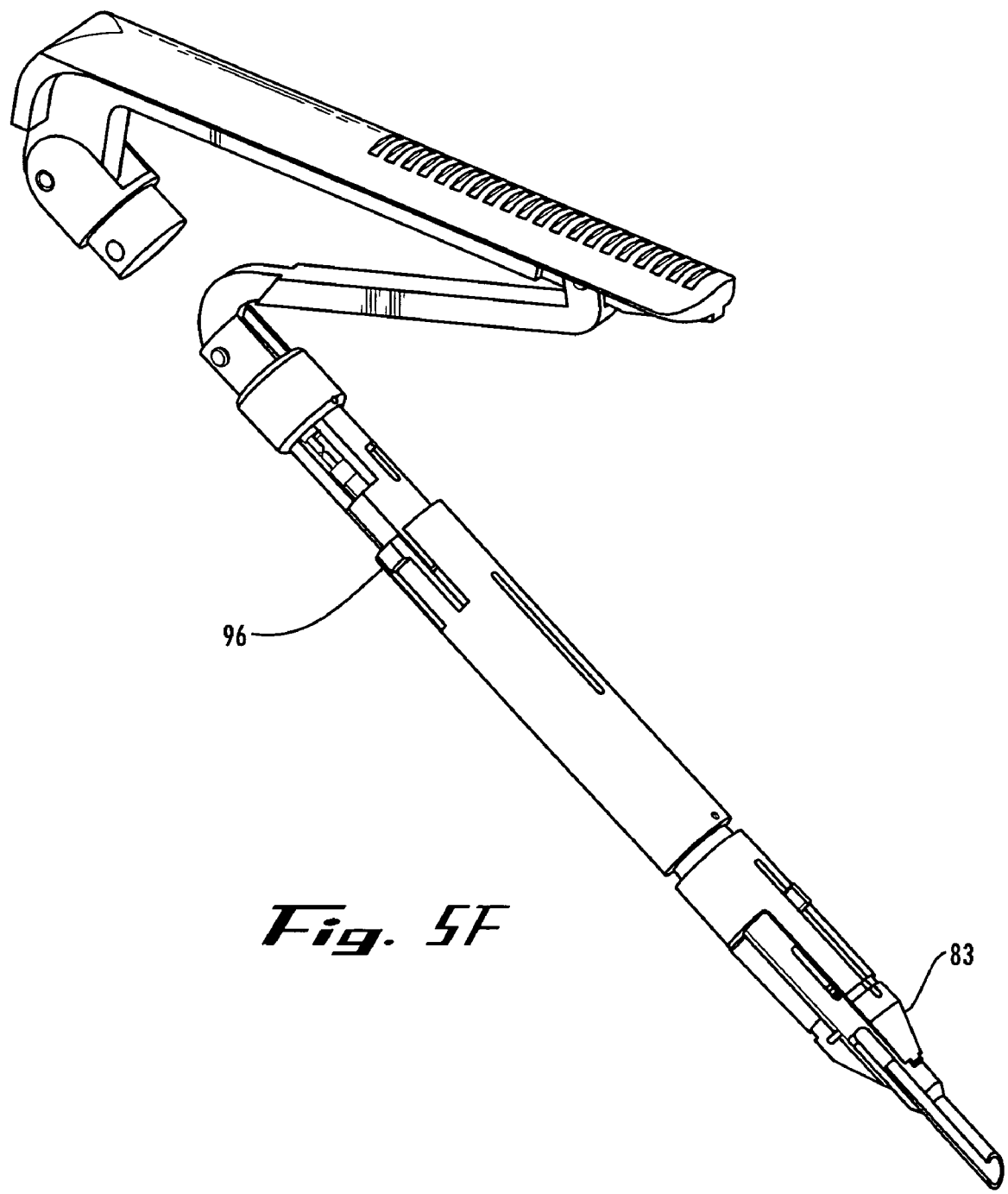
FIG. 5F is another partially exploded view, showing components of the instrument of FIG. 5A or FIG. 5B.

One or more locking member triggers 96 (two triggers 96 are provided in the example of FIGS. 5A and 5F) maintain locking member 83 in the loaded position shown in FIGS. 5A-5B during placement of device 1,1' into an opening of a vessel where the anastomosis is to be formed. Triggers 96 are connected to locking member 83 and slide along with locking member 83, but prevent the locking member from moving any further distally than that shown in FIG. 5A, while each trigger 96 is locked or restrained by a distal end of a slot or opening 97 formed in main body 52. Trigger arms each contain a shoulder or ledge at their proximal ends which abuts against the distal end of the respective slot or opening 97 when the distal portion of actuation link 88 is in contact with the proximal end portion(s) of trigger(s) 96. Trigger arms of triggers 96 are biased radially inward, so that when actuation link 88 is removed from contact with trigger(s) 96, trigger(s) 96 move radially inward, releasing the contact with main body 52, at which time the remaining biasing force on locking member 83 by biasing member 95 drives locking member 83 distally to perform the locking function. The distal end portion of actuation link 88 is dimensioned to maintain the triggers radially outward from their unbiased positions, and in contact with the distal ends of slots or opening 97 when in contact therewith.

Device 1,1, may be loaded and maintained in alignment with instrument 50 by the capture of breakaway tines 20B by tension actuators 55, in a similar manner to that described above with regard to the instrument shown in FIG. 3A. This alignment ensures that the proximal end or surfaces of ring 10 will substantially conform to stop member 70 and that the distal end or surface of locking member 68 will evenly meet the locking members 20L to perform the locking function, as described below. The device 1,1' is slid onto the distal portion 60 until it makes contact with stop member 70. The proximal end 70A of stop member 70 may be beveled to provide a ramping surface against which device 1,1' comes to rest. In this way, stop member 70 not only helps to correctly position device 1,1' in a longitudinal position along the distal portion 60, but also performs a centering function to keep device 1,1' properly centered on the distal portion 60 of deployment device 50.

Once device 1,1' is properly positioned and abutted against stop member 70, locking member 83 is slid proximally (toward handle 85) with respect to tension actuators, causing a further biasing of biasing member 95 and exposing the tension actuators 55 for loading the breakaway tines/engagement portions 20E thereon. After positioning the engagement features 20E over tension actuators 55 (as shown, cross pins, although other engagement features such as clamps, mating threads or other known engagement features could be substituted), locking member 83 is released and returns to the loaded position as it is biased there by biasing member 95, whereby grooves 84 receive the edges of engagement portions 20E to capture the engagement portions 20E and prevent them from coming off cross pins 55, while at the same time capturing device 1,1' to fix its position on device 50, as shown in FIG. 5B. In the capture configuration as described, device 1,1' is securely held by the abutment of ring 10 against stop member 70, and by the tension on breakaway members 20B supplied by tension actuators 55.

Loading a Graft on the Device

Figure 6:
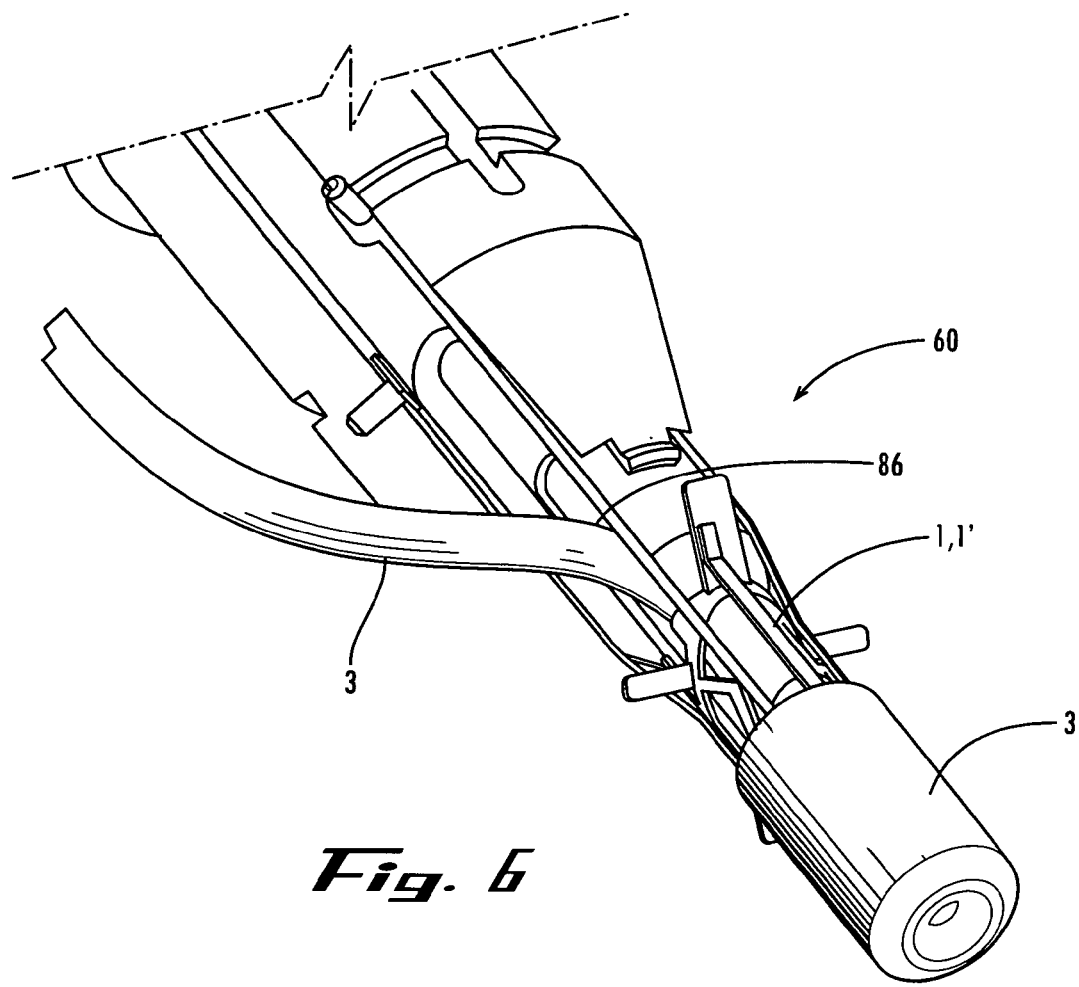
FIG. 6 shows a graft and anastomosis device loaded on a distal end portion of an instrument such as shown in FIGS. 5A and 5B.

A graft may be loaded on device 1,1' either before mounting and capture of the device 1 on instrument 50, or after the device has been captured on instrument 50, due to the access provided by channel 66,86. However, the graft is generally loaded on device 1,1' after capture of device 1,1' on instrument 50, since capture of device 1,1' is preferably performed prior to shipping the product to the end user. FIG. 6 shows a graft 3 which was loaded through slot 86 and fixed to device 1,1', after device had already been mounted on distal portion 60 of instrument 50, for performing a proximal anastomosis of graft 3 with an aortic wall. In this case, an internal mammary artery was used as the graft and so the opposite end of the graft (not shown) is still connected to the vasculature of the patient. Further, this feature would also allow the distal anastomosis of a graft initially having two free ends (such as a saphenous vein graft as one, non-limiting example) prior to the proximal anastomosis of the graft.

Currently known procedures typically require the proximal anastomosis to be performed before the distal anastomosis is performed. This is disadvantageous for at least two reasons. One reason is that surgeons are currently trained to perform the distal anastomosis prior to performing the proximal anastomosis. A second reason is that, depending upon the location of the coronary artery which is being bypassed, it is very frequently necessary to move the heart out of its natural position, such as by elevating it out of the chest cavity to provide access to the site where the anastomosis is to be performed. If the proximal anastomosis must be performed first, this makes it very difficult, if not impossible to accurately measure the length of graft that will be needed to properly perform the distal anastomosis. This is so, because in the displaced position, the heart is not fully perfused, and therefore any measurements made at this time are almost certain to be inaccurate, as the actual distance between proximal and distal anastomosis sites will change when the heart is returned to its natural position and becomes fully perfused, thereby enlarging somewhat. The current invention allows the distal anastomosis to be performed first, after which the heart can be properly positioned and an accurate assessment of the graft length needed can be made before performing the proximal anastomosis.

Therefore, it is often advantageous to perform the distal anastomosis prior to the proximal anastomosis in a cardiac bypass procedure as it is much easier to gauge the correct length to which the graft needs to be cut when the distal anastomosis is performed first since the heart will be normally loaded with blood and the surgeon can get a better approximation of where the locus of the proximal anastomosis will reside after completion of the procedure, which allows a more direct measurement of the length of the graft needed. As noted, the heart very often needs to be displaced to perform the distal anastomosis. By performing the distal anastomosis first, the heart can then be repositioned to its natural location and orientation, thereby making it much easier for the surgeon to visualize and directly measure or approximate the length of graft needed to reach the proximal anastomosis site. Since most surgeons traditionally perform the distal anastomosis first, even when using suturing methods, they will be more inclined to accept a procedure where distal anastomosis can be performed first.

Figure 7:
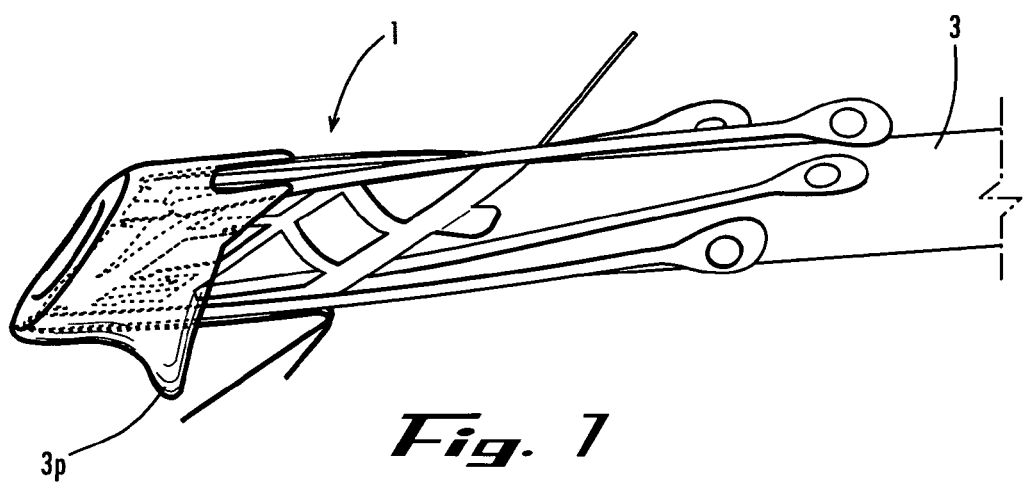
FIG. 7 shows a graft having been loaded and everted over a device according to the present invention.

FIG. 7 shows an example of a graft 3 that has been loaded prior to mounting and capturing the device 1,1' on the deployment instrument 50, for simplicity of illustration. However, loading of the graft after capture of the device is performed generally in the same manner as is now described. A free end of graft 3 is passed through the interior of the device 1,1' and then everted over the proximal end of the device 1,1' as shown in FIG. 7. Upon eversion of the free end, tines 14 pierce the external wall of the everted end thereby holding the end in the everted configuration. In the case where longer graft tines are to be employed, where the tines pass all the way through the walls of the everted end, the tines may need to be further bent over after the eversion, to facilitate insertion of the graft and device through the opening in the target vessel for performance of the anastomosis. However, in the example shown in FIG. 7, tines 14 do not penetrate through the inner wall of the everted graft 3 and do not need to be further bent over after the eversion.

Because device 1,1' has an angled distal surface (formed by ring 6) as described above, and graft 3 is generally cylindrical, having a substantially circular cross section, the ellipsoidal surface formed by the angled distal surface of device 1,1' causes an uneven, or misaligned deformation of graft 3 where it is everted over device 1,1' which results in a puckering away from the device 1,1' in the end of the graft adjacent the most distally extending portion of the distal end of device 1,1', as shown in FIG. 7. The degree or amount of pucker is dependent upon the degree of angulation of the distal end of device 1,1' from normal to the longitudinal axis L. If the distal end of device 1,1' were normal to the longitudinal axis L, its surface would form a circle and would not pucker the graft 3 end at all. To reduce puckering, FIG. 1A shows an optional modification to ring 6 which includes ring portion 6A. Ring portion 6A effectively reduces the initial angulation of the distal end of device 1 by extending the heel of the device further distally than that of the example shown in FIG. 7. Thus for example, if the main ring 6 of the device forms an angle of about 60 degrees to the normal, optional ring portion 6A may reduce the initial angulation to about 45-50 degrees to the normal. The device 1' shown in FIG. 1B may be similarly optionally modified.

Figure 1E:
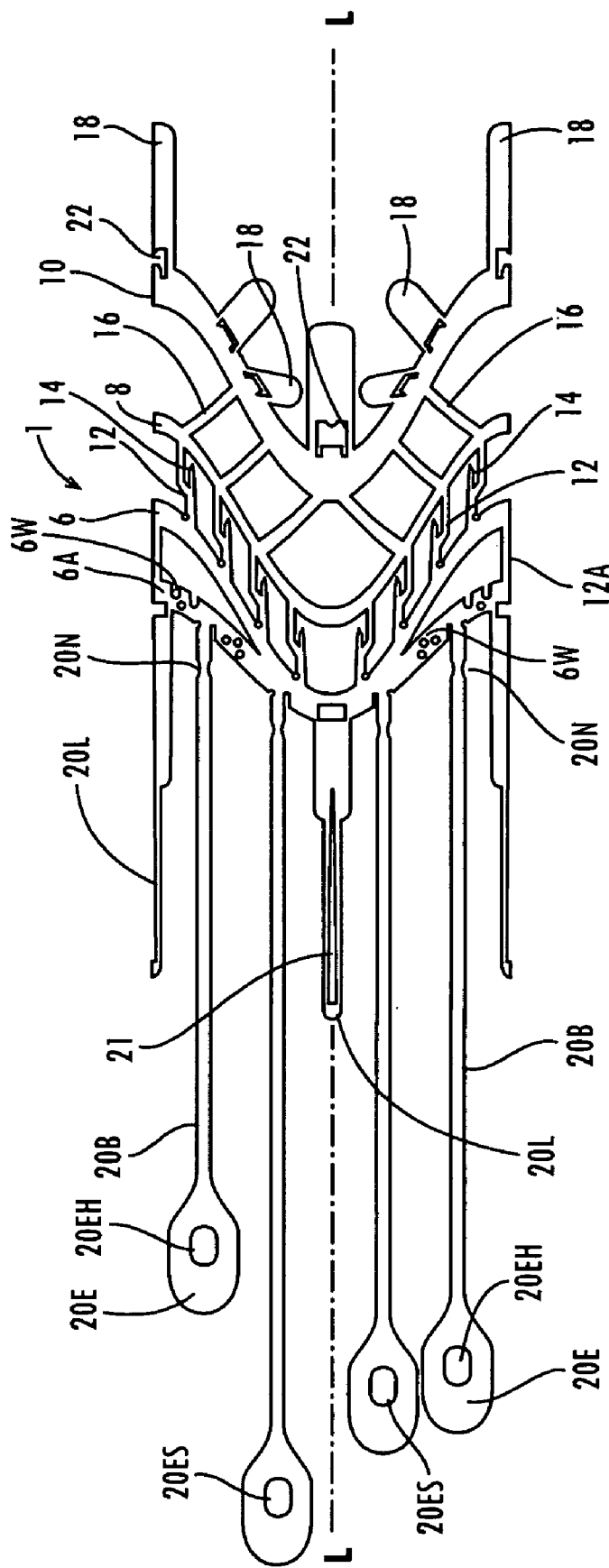
FIG. 1E shows another example of an anastomosis device, according to the present invention.

Optional ring portion 6A may be connected to ring 6 by substantially rigid struts 12A, as shown in FIG. 1A, in which case ring 6A does not collapse against ring 6 during deployment and buckling of struts 12 and 16. Alternatively, ring 6A may not be connected by struts to ring 6, as shown in FIG. 1E. In this arrangement, the extending portions of ring 6A may be weakened by providing weakened sections 6W including cutouts, holes, slots, or other means of causing these sections to bend under less force than the remainder of ring 6A. Further, the engagement portions 20E of the breakaway tines 20B which are connected to the non-extending portion of ring 6A (i.e., the portion of ring 6A which joins with ring 6) are provided with elongated openings or slots 20ES relative to the openings or holes 20EH in the engagement portions 20E of the breakaway tines 20B that connect to the extended, weakened portions of ring 6A. By this design, when tension is applied by tension actuators, it is initially only applied though breakaway tines having openings 20EH. Upon collapse of the extending portions of ring 6A, tension actuators then also make contact with the ends of elongated openings 20ES, so that tension is applied evenly to all breakaway tines 20B to collapse the entire rings 6, 8 and 10 toward one another. Thus, initially, the extending portion of ring portion 6A may be compressed against ring 6 prior to buckling struts 12 and buckling/bending struts 16 to complete the deployment of device 1,1'. Further alternatively, the extending portion of ring portion 6A may not be connected to breakaway struts 20B so that ring portion 6A maintains the initial angulation of the distal end of device 1,1' even after full deployment.

For loading graft 3 onto device 1,1' when device 1,1' has already previously been captured by deployment tool 50, as shown and described above with regard to FIG. 6, graft 3 is loaded through slot 66,86, as noted above, passed through device 1,1' and everted thereover. Once the graft 3 has been loaded and everted on a device 1,1' the assembly is ready for the performance of an anastomosis.

Performing the Anastomosis

The present invention is applicable for performing a variety of anastomosis procedures, including coronary artery bypass grafting. One or more anastomoses are performed on a target vessel within a patient, by connecting one or both ends of a graft to the target vessel. The following description pertains to a specific, non-limiting application of the present invention in performing an angulated end-to-side anastomosis of a proximal end of a graft to the wall of the aorta.

The description begins with the surgical site having already been prepared for performance of the anastomosis. The anastomosis can be performed with the heart stopped and the patient on cardiopulmonary bypass or during a beating heart bypass procedure. Examples of grafts appropriate for use in performing an anastomosis include an internal mammary artery having only one free end (the end on which the anastomosis is to be performed), a saphenous vein graft or radial artery graft having two free ends (in which case it is possible to perform the distal anastomosis first, if desired, as noted above) or some other suitable graft.

After selection and preparation of the graft to be used, the proximal end of the graft 3 is loaded and everted onto the device 1,1' by passing the proximal end 3 through the interior of the device 1,1 and then everted over the proximal end of the device 1,1' as shown in FIG. 6. If elongated graft tines are employed, which pierce and extend through the entire wall of the graft, the tines are preferably further bent over, after the eversion. For this example, however, shorter graft tines 14 are employed, which do not protrude through the inner wall of the everted graft 3. The shortened tines 14 pierce into the wall, but do not extend through and out of the wall. If no graft tines are used, the appearance will be the same as shown in FIG. 6. As described above, tension actuators 55 maintain device 1,1' in abutment against stop member 70, thereby capturing the device 1,1' and graft 3 in a position ready to be deployed to perform the anastomosis. Once the graft 3 has been loaded and everted on captured device 1,1', as described, an aortotomy punch 160 as shown in FIG. 8 (available from Guidant, Santa Clara, Calif.) or other cutting or punching instrument may be used to punch a hole in the wall of the target vessel (e.g., aorta) at the site that the anastomosis is to be performed.

Aortotomy punch 160 provides an initial blade stab with a retracting rotary punch that creates a circular aortotomy 162 in target vessel 164, the aortotomy having a specific diameter that is matched to the outside diameter of the graft 3 everted over the device 1, see FIGS. 8 and 9. For a beating heart procedure, the aortotomy is temporarily sealed, such as by application of finger pressure by the surgeon, to prevent blood loss while the graft assembly is approximated to the aortotomy 162. The finger pressure is then released and the graft/device are inserted into the aortotomy, as shown in FIG. 10, preferably using a rolling or rotating motion which allows a rapid insertion to stop the majority of blood flow from the aortotomy 162. The graft/device may be initially inserted at an orientation which is substantially perpendicular to the aorta, as the substantially cylindrical cross-section of device 1,1' perpendicular to its longitudinal axis L, facilitates the best fit and easiest insertion through the aortotomy 162. The insertion is made in this orientation until the leading or most distally extending external tine or tines 18 abut the external wall of the target vessel.

Next, deployment instrument 50 is tilted or rotated, to a position which causes all of the tines 18 to substantially abut the external wall of the target vessel, as shown in progress in FIG. 10, at which time the deployment of the device 1,1' can be performed. Although a circular aortotomy punch is currently used to form the aortotomy, as described above, it is noted that the angulation of device 1,1' will exert some stress on the periphery of the aortotomy, as it must be stretched to accommodate the larger cross-sectional area of the elliptical cross section of the tilted device 1,1'. For this reason, an elliptical aortotomy punch (not shown) may be employed, which may function the same as the punch 160 described with regard to FIG. 8, but which has an elliptically shaped cutting edge, rather than the circular edge provided in punch 160. By orienting the elliptical aortotomy so that the major axis of the elliptical cut aligns with the direction of tilt or angulation, this will provide some stress relief to the host wall as the device is rotated into the angulated position from which it is to be deployed.

Figure 11A:
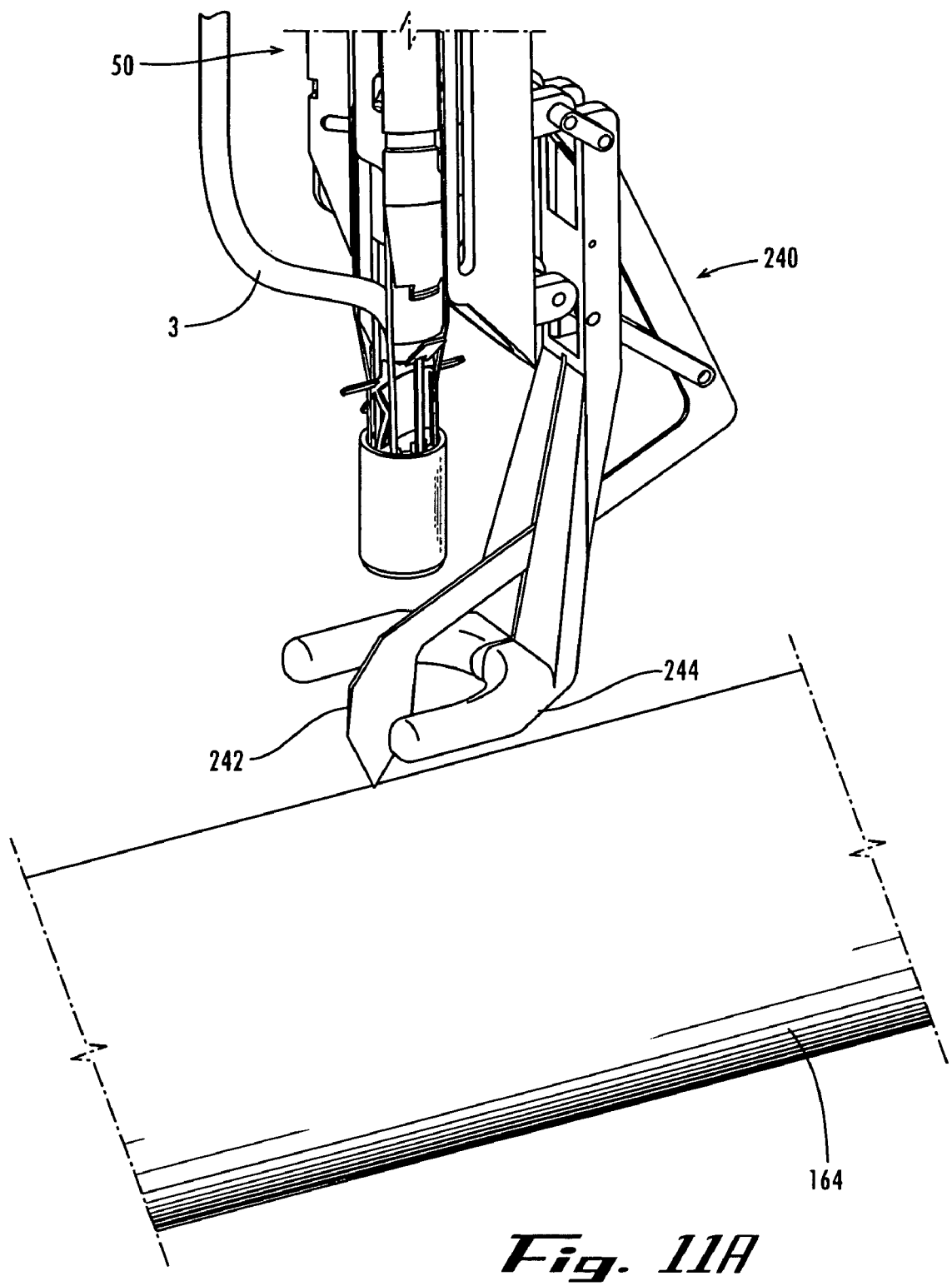
FIG. 11A is a partial view of a deployment device with attached cutting tool, shown in the cutting configuration.
Figures 11B, 11C:
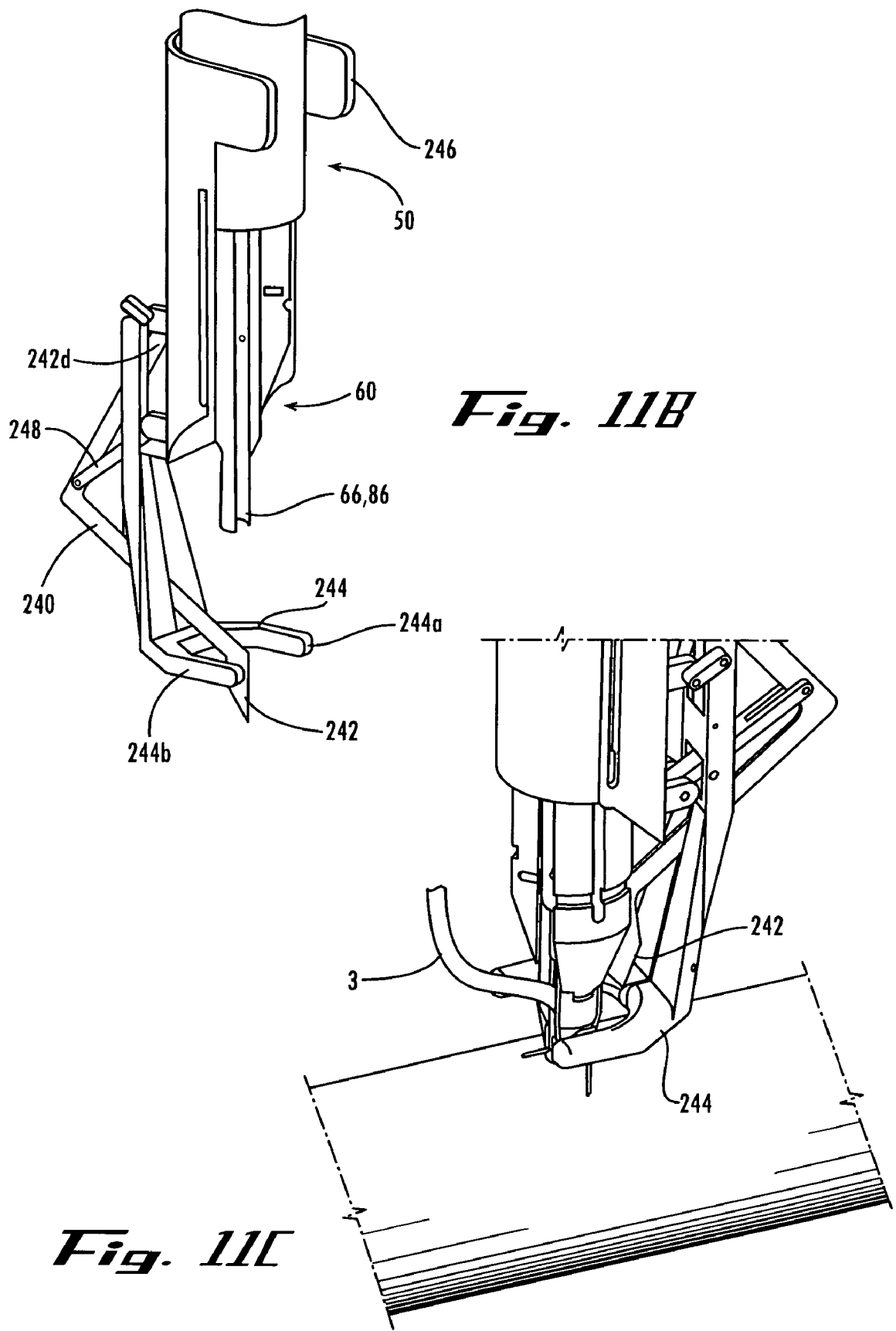
FIG. 11B is a full schematic, perspective view of the cutting tool of FIG. 11A attached to a deployment instrument.
FIG. 11C shows the arrangement of FIG. 11A with blade retracted, allowing insertion of a device by the deployment tool.

Further alternatively, rather than using a circular, elliptical or other shape aortotomy punch 160 in the above-described method, a slit may be cut into the target vessel using the blade 242 of cutting device 240, as shown in FIG. 11. Although device 240 may be formed integrally with a delivery device 50 of any type described above, it is preferred to make device 240 removable from delivery device 50 to facilitate loading device 1,1' as well as everting graft vessel 30, such as according to processes described above, prior to attaching device 240 to device 50. In the example shown, device 240 is adapted to clip on to the body of device 50, and is provided with a pair of clip arms 246 (FIG. 11B) which are somewhat deflectable to allow the body of device 50 to be positioned therebetween. A spring force is applied by arms 246 against the body of device 50 as they are deflected during installing device 240 on device 250, the spring force being generated upon deflection of arms 246 as the body of device 250 deflects them. The spring force, together with frictional forces between arms 246 and the body of device 50 maintains device 240 in an integrated position as shown in FIGS. 11A-11C. Of course, other alternative connecting means could be provided for mounting a removable device 240 to a device 50 as would be readily apparent to those of ordinary skill in the art, such as by attaching by screws, or other removable attachment means.

Blade 242 may be a sharp-tipped, razor blade-like implement or other sharp cutting instrument designed to form a slit in the target vessel, of a length which has been determined to be sufficient to insert the device 1,1' and everted graft vessel 30 through to accomplish the anastomosis. Device 240 is provided with an extending foot 244 which is adapted to be placed in contact with the target vessel when blade 242 has pierced the target vessel sufficiently to form the desired slit, acting as a stop to indicate when the slit has been completed. Arms 244a and 224b that are extensions of foot 244 act as a site to properly position and target blade 242 to form the slit at the desired target location, and also function to target further steps in the anastomosis process.

By maintaining pressure against the distal end 242 of the arm extending from blade 242, such as by applying finger pressure thereto (alternatively, a tension spring (not shown) may be connected to linkage 248 to bias blade 242 to the extended position) blade 242 is maintained in the extended position shown in FIGS. 11A-11B. In such position, the operator of the integrated device 50,240 then advances the integrated device to apply blade 242 to a location on the target vessel where it is desired to perform the anastomosis. Blade 242 is inserted into the target vessel and the integrated device is advanced toward the target vessel until a sufficient slit length is achieved, typically when foot 244 contacts the target vessel.

By maintaining contact between foot 244 and target vessel 164, this ensures that device 50 maintains device 1,1' and the everted end of graft vessel 3 in alignment with the slit in the target vessel. The operator then releases the pressure against end 242d and advances device 50 further toward the target vessel to insert device 1,1' and everted graft end 3 into the slit. Blade 242 is mounted to device 240 via a linkage 248 (e.g., such as the four bar linkage shown) which causes blade 242 to retract both proximally and radially away from the slit/anastomosis site as device 50 and the main body portion of device 240 which is clipped to device 50, are advanced toward the target vessel, as shown in FIG. 11C. This leaves a clear path for the insertion of device 1,1' and everted graft vessel 3 by delivery device 50 which is held in alignment with the slit, as guided by foot 244. Once device 1,1' and everted graft end 3 are inserted into the slit, the remainder of the anastomosis proceeds in the same manner as described above with regard to the process that employed the aortotomy punch 160. Device 240 simplifies the earlier described approach, by doing away with the need for aortotomy punch 160 and thus providing a "one shot" technique.

The tilted or angulated orientation of the device 1,1', as described, is the orientation in which the graft 3 will be anastomosed to the target vessel 164 by deployment of device 1,1'. As mentioned above, either an instrument having a flat or straight tip, such as shown in FIG. 5A may be used, or an instrument 50 having an angled distal tip portion, such as shown in FIGS. 3A and 5B, for example, may be employed. The distal tip portion 60 of the angled instrument 50 may be angled from above zero degrees to about 60 degrees, and will preferably be angled by a complementary angle to the angle that the graft will form with the target vessel after completion of the anastomosis (i.e., angle of instrument=90 degrees minus angle between graft and target vessel). An angled deployment tool/instrument, as described may also be used in conjunction with device 240, in the same manner as described above with regard to its use with a straight deployment tool.

Figure 12:
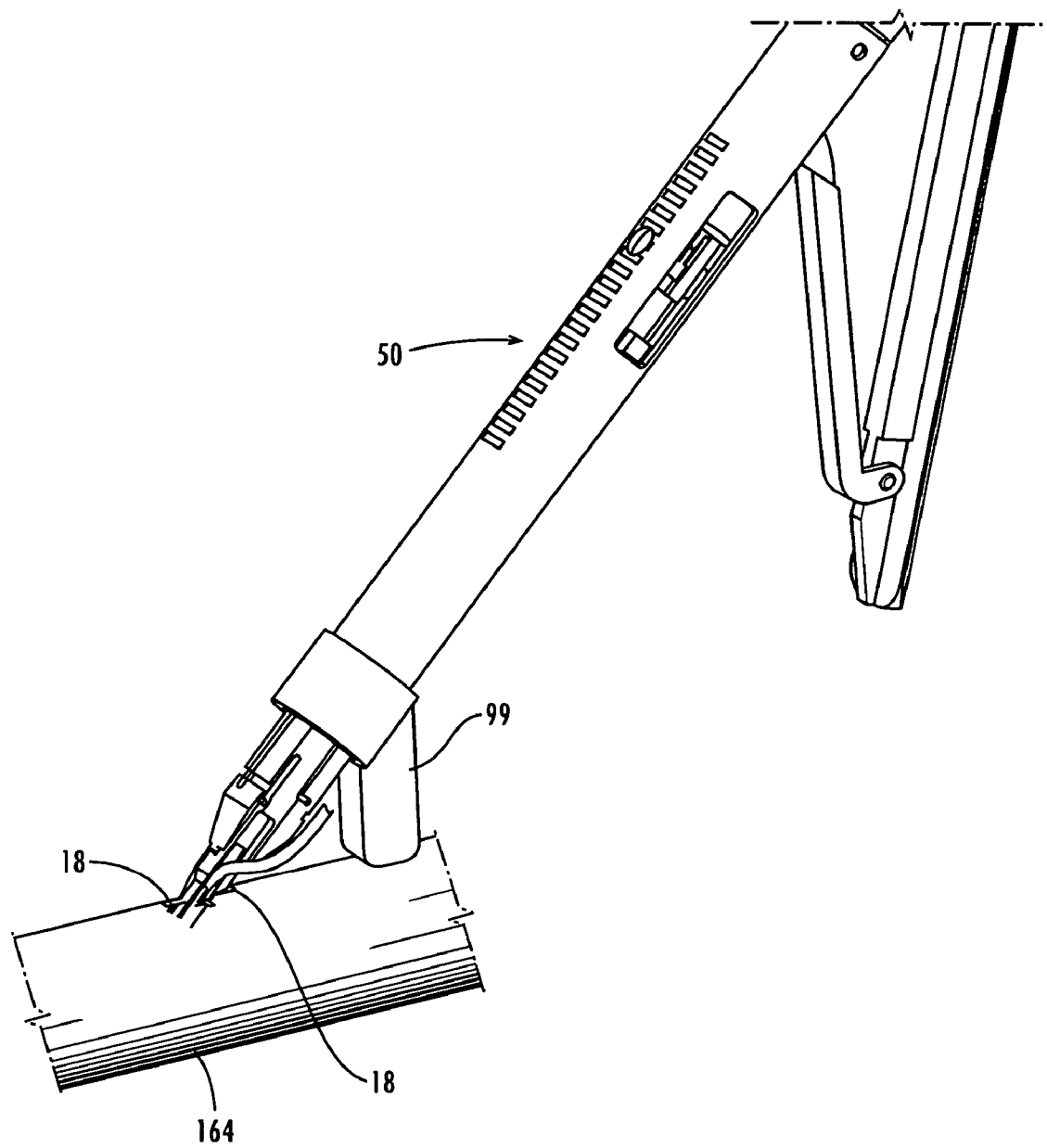
FIG. 12 is a schematic partial view showing insertion of a graft and anastomosis device into an opening in a target vessel using a deployment instrument that includes a rotation stop.

Optionally, the deployment instrument 50 (either straight or angled instrument) may be provided with a rotation stop 99, such as shown in FIG. 12, which is configured to abut the host (target vessel 164) when instrument 50 has been rotated through an angle sufficient to align the external tines 18 into abutment with the external wall of the host.

The angulation of device 1,1' (i.e., angulation of rings with respect to perpendicular line to longitudinal axis L) is matched to the desired angulation of the junction of the graft 3 to the host 164 after performance of the anastomosis. Generally, the angulation will range from about 30 degrees to about 45 degrees. Certainly the angulation can be made greater than 45 degrees, but the benefits of performing an angulated anastomosis begin to significantly decrease with angles greater than about 45 degrees. For angles smaller than 30 degrees, the functionality of the device is more difficult to maintain with the increased angles of the rings, and such a sharp angle begins to approach an anastomosis that functions about the same as a side-to-side anastomosis, so that it would make sense to perform a side-to-side anastomosis for angles less than about 30 degrees.

To deploy the device 1,1' using instrument 50 shown in FIG. 3A, handle 56 is initially slid back toward handle 54, which is fixed relative to stop member 70. Handle 56 is connected with tension actuators 55, as noted above. Therefore, as handle 56 is retracted toward handle 54, tension actuators 55 increase the tension applied to breakaway tines 20B. For deployment of a device 1,1' employing a distal ring angle reduction portion 6A which is to be collapsed or compressed to conform to the angulation of the remainder of the device 1, tension actuators initially focus the increased tension application to breakaway tines 20B which are most closely connected to portion 6A in areas where portion 6A is separated from ring 6, as also noted above.

After initially collapsing portion 6A against ring 6, as described, the deployment of this variation is essentially the same as deploying a device 1,1' which lacks portion 6A, as well as a device 1,1 which includes portion 6A but does not have breakaway tines connected thereto or a device 1,1' which has rigid struts 12A joining ring portion 6A and ring 6 so that ring portion 6A is not to be collapsed against ring 6, so that the angulation of portion 6A will remain even after deployment of the device 1,1'. For any of these variations, continued application of tension through tension actuators 55 compresses device 1,1' to first buckle buckling tines 12 and then struts 16.

Figure 13A:
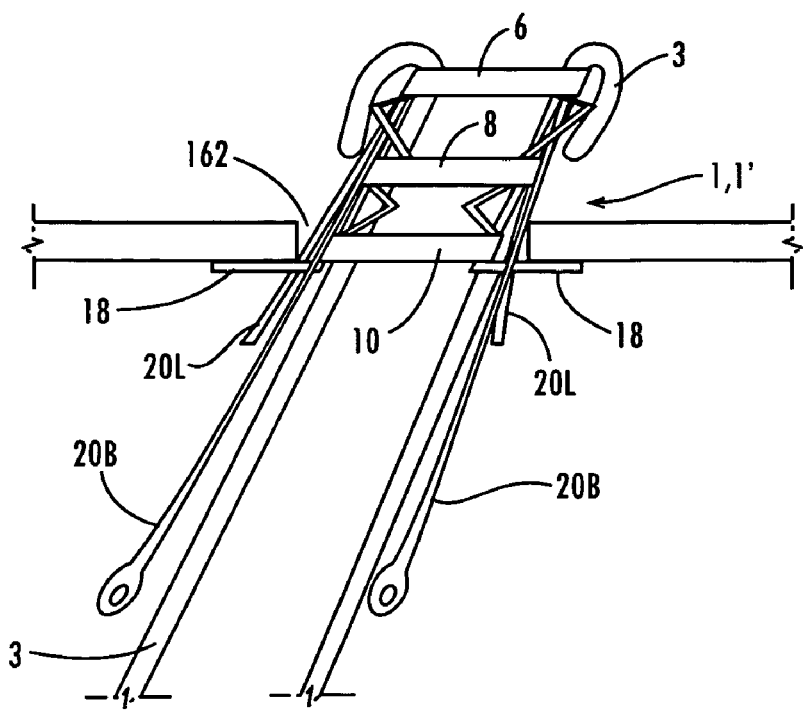
FIG. 13A is a sectional schematic view of a graft and anastomosis device having been inserted into a target vessel and after optionally tilting the deployment instrument to align the external tines in substantial abutment with the external wall of the target vessel.
Figure 13B:
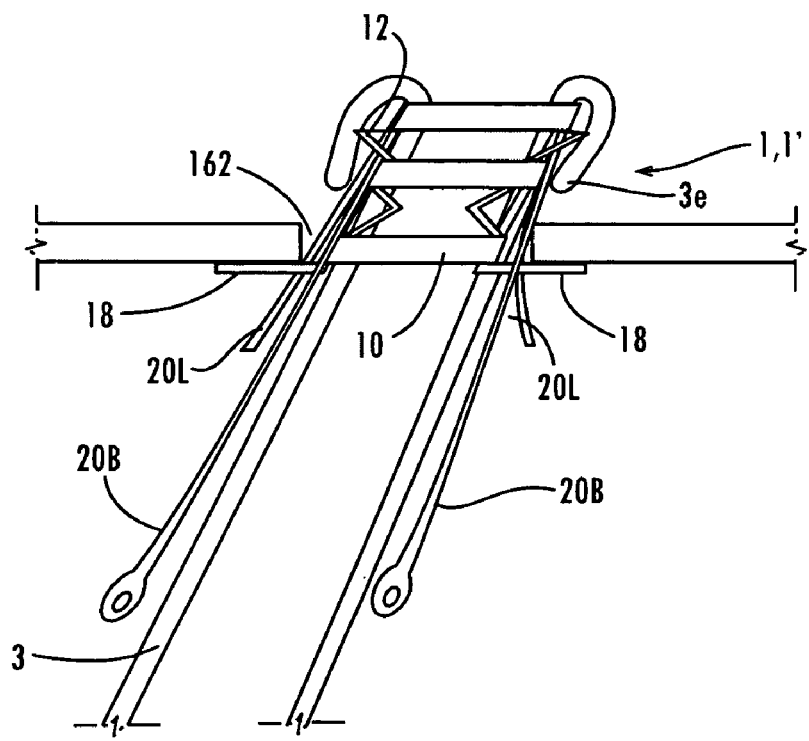
FIG. 13B is a sectional schematic view of the graft and anastomosis device of FIG. 13A after buckling the buckling section of the anastomosis device.
Figure 13C:
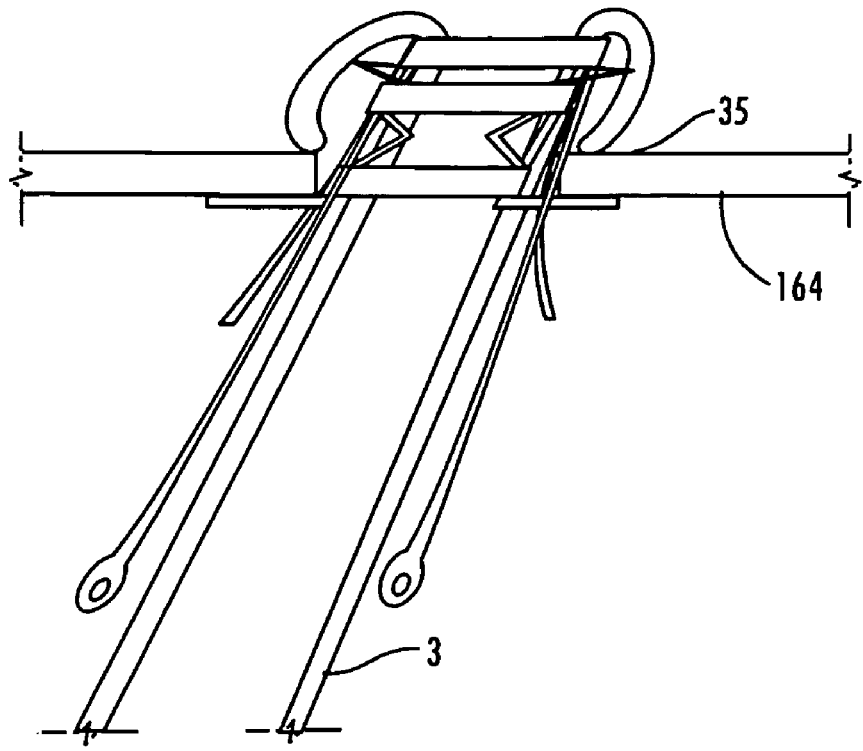
FIG. 13C is a sectional schematic view of the graft and anastomosis device shown in FIG. 13B after having partially collapsed the proximal end section and after beginning to lock the locking tines.
Figure 13D:
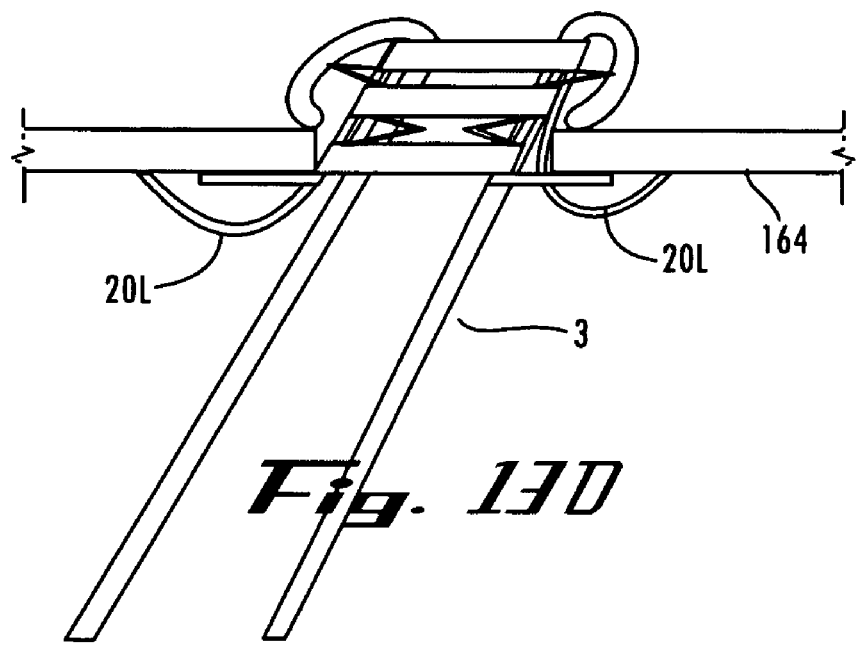
FIG. 13D is a sectional schematic view of the graft and anastomosis device shown in FIG. 13C after having locked the locking tines.
Figure 13E:
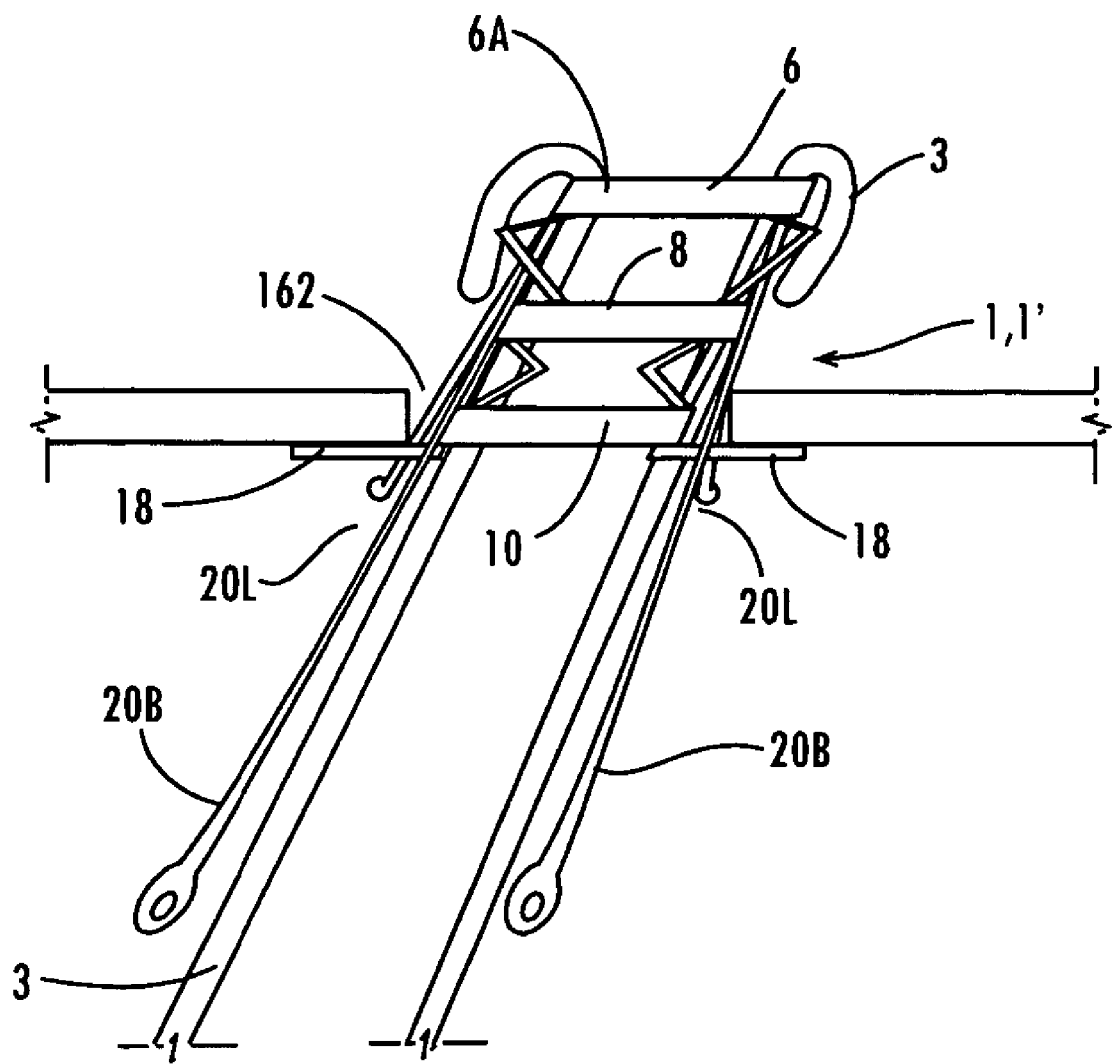
FIG. 13E is a section schematic view of a graft and anastomosis device having been inserted into a target vessel, tilted to align the external tines in substantial abutment with the external wall of the target vessel, and after an optional compression step that collapses a ring portion used to prevent or reduce puckering of the everted end of the graft.

FIGS. 13A-13D (FIG. 13E shows an optional stage) schematically show the various stages of buckling, compressing and locking that are performed in deploying a device 1,1' according to the present invention. For purposes of clarity, the deployment device 50 has not been shown in FIGS. 13A-13E. In FIG. 13A, the graft 3 and device 1,1' are shown after insertion into the aortotomy 162 and tilting the instrument 50 to align the external tines 18 in substantial abutment with the external wall of the aorta, prior to drawing handle 56 toward handle 54. Initially upon drawing handle 56 toward handle 54, the ring portion 6A is drawn against ring 6 by collapsing struts 12A when deploying a device 1 having a ring portion 6A which is desired to reduce the angle of the distal end of device 1 only temporarily (see FIG. 13E). Continued application of tension through breakaway tines 20B causes the buckling section between rings 6 and 8 to collapse or buckle, as shown in FIG. 13B. Due to the partially bent configuration of the struts 12, a controlled direction of buckling is assured which causes a mushroom-shaped configuration to result as shown. The buckled configuration of the buckled struts 12 forms an internal retaining structure, which is drawn to provide a compression force of the graft tissue against the internal aortic wall. The shape and direction of buckling of struts 12 are advantageous in that they further evert the proximal end of the graft at 3e so that the intima of the graft 3 approximates the intima of the target vessel 164 in preparation for forming an intima to intima anastomosis. The further eversion 3e of the graft also assures that there will be no metal contacting either the intima of the aorta or the intima of the graft at the site of the anastomosis, thereby assuring a more reliable seal and more reliable healing.

As the handle 56 continues further in its travel toward handle 54, the struts 16 of the strut section begin to collapse, as shown in FIG. 13C, as the breakaway struts are pulled along by tension actuators 55 toward handle 54 causing a compressive force between ring 6/6A (attached to breakaway struts 20B) and ring 10 (abutting stop member 70). The collapse of the strut section draws the graft 3 and target vessel 164 together with a sufficient force to form a successful seal 3s between the two, while not compressing the anastomosis with too great a force to potentially cause damage to the living tissue. As such, the collapse of the struts 16 draws the rings 8 and 10 closer together, which effectively also draws the buckled struts 12 closer to ring 10, thereby compressing the everted face 3e of the graft and the wall of the aorta.

After collapse of the struts 12 and 16, handle 57 is slid distally away from handle 54, while at the same time maintaining tension with handle 56, to perform the locking operation. As handle 57 moves distally, locking driver 68 moves distally with it, bending over the locking tines 20L, as shown in FIG. 13D, as it drives toward the distal end of device 1,1', thereby firmly locking the relative positions of the rings 6, 8 and 10, to set the compression force maintaining the anastomosis. The locking tines 20L may be provided with sharp points, barbs, or other configuration at their distal ends to facilitate piercing or other mechanical engagement of the outer wall of the aorta.

Compression spring 74 of the deployment device acts as a force limiter on the locking driver 68. After locking of the device has been accomplished, handle 56 is further drawn toward handle 54 to apply sufficient tension to breakaway tines 20B to cause breakaway tines to break away at the necked regions 20N. Necked regions 20 are configured to break at a predetermined loading force to limit the amount of compression of the device 1,1' against vessel 3 and vessel 164 applied by the anastomosis. For example, the breaking force may be in the neighborhood of about sixteen+2 pounds. In another example, the buckling of tines 12 may occur with about 3 pounds of tension, the compression of struts 16 and locking of locking tines 20L may occur under about 5 pounds of tension, and the break away of breakaway tines may occur at about 8 pounds of tension. However, any and all of these actions can be adjusted to occur at different tension ratings, with the caveat, that deployment of the device 1,1' should not require so great a tension/compression force to cause tissue damage. After the breaking away of breakaway tines 20B, the entire device 50 (along with substantially all of each breakaway tine 20B) can be withdrawn from the site of the anastomosis, thereby completing the anastomosis. Thus, the deployment tool 50 is removed by sliding the distal end portion 60 out from inside device 1,1' and the graft 3 is slid out of the groove 66, leaving device 1 and graft 3 undisturbed at the site of the anastomosis.

To deploy the device 1,1' using instrument 50 shown in FIG. 5A or 5B, handle 85 is squeezed toward the main body 52 of instrument 50 As handle 85 travels toward main body 52, the proximal end of linkage 87 is forced further proximally with respect to main body 52. Proximal movement of the proximal end of linkage 87 draws actuation linkage 88, clutch member 89, shaft 90 and tube 81 proximally with respect to main body 52 and fixed tube 82, thereby compressing rings 6, 8, 10 (and optionally, 6A) together, as was described previously and is illustrated in FIGS. 13A-13E, as the tension applied to breakaway tines 20B by tension actuators, which are fixed to tube 81, draw device 1,1' against stop member 70.

As the handle 85 continues further in its travel towards body 52, and the struts 12,16 have been buckled, sufficient force is generated to cause clutch member 89 to fail, thereby breaking or separating the proximal and distal end portions of clutch member 89. This separation temporarily relieves tension on shaft 90 until shaft 90 is engaged by the distal end portion of actuation link 88 after shaft 90 slides through slot 93. Additionally, as linkage member is drawn proximally by actuation of handle 85 as noted, the distal end portion of actuation link 88 loses contact with triggers 96.

Upon losing contact with triggers 96, triggers 96 travel radially inwardly, breaking contact/abutment with the slot ends in main body 52, thereby releasing locking member 83 to be driven against locking tines 20L by the biasing force applied by biasing member 95. Continued movement of handle 85 toward main body 52 applies increasing tension on tension tines through actuation link 88, shaft 90 and tube 81, until the tension is sufficient to cause breakaway tines to break away at the necked regions 20N. Necked regions 20 are configured to break at a predetermined loading force to limit the amount of compression of the device 1,1' against vessel 3 and vessel 164 applied by the anastomosis. As an example, struts 12,12' may buckle at about three±one pounds, struts 16 may buckle at about eight±one pounds, the clutch member 89 may break at about twelve±two pounds and breakaway tines may break away in the neighborhood of about sixteen±two pounds. The breakaway tines 20B act as a force limiter to limit the amount of compression force applied to the device 1,1' in forming the anastomosis. As in the previous example, any and all of these actions can be adjusted to occur at different tension ratings, with the caveat, that deployment of the device 1,1' should not require so great a tension/compression force to cause tissue damage.

After the breaking away of breakaway tines 20B, the entire device 50 (along with substantially all of each breakaway tine 20B) can be withdrawn from the site of the anastomosis, thereby completing the anastomosis. Advantageously, tube 81 retracts from device 1,1' during application of tension, thereby leaving no chance of device 1'1' becoming caught on tube 81 after it is compressed. Thus, the deployment tool 50 is simply removed form the site of the anastomosis by sliding the graft 3 out of the groove 86, leaving device 1,1' and graft 3 undisturbed at the site of the anastomosis.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A device for use in making an angled anastomosis between first and second tubular fluid conduits in the body of a patient, said device comprising:
    a unitary structure having a main body disposed annularly about a longitudinal axis, having a proximal end portion with a proximal end, and a distal end portion with a distal end, and adapted for passing the first tubular conduit through an annulus defined by the main body;
    an exterior of said main body configured to be inserted through an opening in the second tubular conduit;
    at least one first member extending radially from said proximal end portion and, in an undeformed configuration, angled toward a proximal direction of said device, relative to said longitudinal axis, and at least one second member extending radially, in said undeformed configuration, from said proximal end portion and angled toward a distal direction of said device, relative to said longitudinal axis, said members extending from said proximal end portion configured to abut against an external wall of the second conduit upon angulation of said main body with respect to a wall of the second tubular conduit;
    locking members fixed to said distal end portion and slidably received by said proximal end portion, wherein, upon buckling of said distal end portion, free ends of said locking members slide to extend proximally of said proximal end portion;
    said distal end portion being configured to buckle in response to axial compression of said device, wherein said distal end portion plastically deforms and is incapable of passing through said opening after buckling and exerts a compressive force between the first conduit and the wall of the second conduit upon buckling, while maintaining the angled configuration of the main body with respect to the second conduit.

2. The device of claim 1, said distal end portion further comprising:
    conduit retainers, wherein, upon passing the first conduit through said main body, a free end of the first conduit is everted over a distal end of the device and retained by said conduit retainers, and wherein said distal end is angled with respect to a normal to the longitudinal axis.

3. The device of claim 2, wherein said conduit retainers comprise graft tines.

4. The device of claim 1, wherein said distal end portion comprises buckling struts configured to ensure buckling in a radially outward direction upon application of a compressive force thereto.

5. The device of claim 1, wherein said at least one first member and at least one second member extending from said proximal end portion comprises a plurality of at least one of said first and second members extending from a proximal end of said device and oriented substantially parallel to the proximal end.

6. The device of claim 1, wherein said proximal end being uniformly angled with respect to a normal to said longitudinal axis, when said device is in an undeformed configuration, and said proximal end also being angled with respect to a normal to said longitudinal axis when in a deformed, deployed configuration.

7. The device of claim 1, wherein said proximally extending free ends of said locking members are adapted to be bent over against said proximal end portion and the external wall of the second conduit to lock the relative position of said proximal and distal end portions.

8. The device of claim 1, wherein said proximal end portion is variably collapsible to accommodate varying wall thicknesses, so as to make said device adaptable for joining the first conduit to various second conduits having varying wall thicknesses.

9. The device of claim 8, wherein distal and proximal ends of said device are uniformly angled with respect to a normal to the longitudinal axis by a predefined angle, and wherein said distal and proximal ends substantially maintain said predefined angle after buckling of the distal end portion and collapsing of the proximal end portion.

10. The device of claim 9, wherein said predefined angle is in the range of about 30 degrees to about 45 degrees.

11. The device of claim 10, wherein said angulation of the main body and said substantial maintenance of the predefined angles of said distal and proximal ends maintains the first tubular conduit at substantially said predefined angle with respect to the second fluid conduit upon completion of the anastomosis.

12. An anastomosis device comprising:
a unitary structure having a main body having an outside diameter adapted to pass through and form a close fit with an opening formed in a wall of a conduit to be joined by anastomosis;
said main body defining an annulus having an inside diameter, said annulus extending longitudinally through said body along a longitudinal axis thereof;
said body having proximal and distal end portions angled at non-zero angles with respect to a normal to the longitudinal axis and with respect to the longitudinal axis, said proximal and distal end portions having a proximal and distal end, respectively, said distal ends being uniformly angled with respect to said normal and said longitudinal axis and said proximal ends being uniformly angled with respect to said normal and said longitudinal axis;
an extension portion extending from said proximal end portion, having a length sufficient to span the length of said main body, and configured to be incapable of passing through the opening;
locking members fixed to said distal end portion and slidably received by said proximal end portion, wherein, upon buckling of said distal end portion, free ends of said locking members slide to extend proximally of said proximal end portion; and
conduit retainers on said distal end portion adapted to retain a free end portion of a conduit having been passed through said annulus and everted over said proximal end portion.

13. The device of claim 12, wherein said main body is generally in the shape of an oblique cylinder.

14. The device of claim 12, wherein said distal end portion is configured to ensure outward buckling in response to axial compression of said device, and wherein said distal end portion is incapable of passing through the opening after buckling and exerts a compressive force toward said extension portion.

15. The device of claim 14, wherein said distal end portion is adapted to further evert the conduit retained by said conduit retainers upon buckling.

16. The device of claim 12, wherein said proximally extending free ends of said locking members are adapted to be bent over against said proximal end portion to lock the relative position of said proximal and distal end portions.

17. The device of claim 12, wherein said proximal end portion is variably collapsible to accommodate varying wall thicknesses that occur among different patients.

18. A device for use in making an angled anastomosis between tubular fluid conduits in the body of a patient, said device comprising:
a unitary structure having a main body disposed annularly about a longitudinal axis and having first and second end portions each encircling an annulus that the longitudinal axis passes through and angled with respect to a normal to the longitudinal axis, said first end portion having a first end angled with respect to the normal to the longitudinal axis, with a location on said first end that is furthest from said normal to the longitudinal axis at a location passing through said main body being opposite to a location on said first end that is nearest to said normal to the longitudinal axis at said location passing through said main body;
a plurality of members extending radially outwardly from said first end portion;
said second end portion having a plurality of spaced struts adapted to buckle in a radially outward direction upon axial compression of said device, wherein said struts are plastically deformed during buckling; and
a plurality of elongated members extending from said second end portion toward said first end portion and adapted to apply a compressive force to said second end portion to buckle said spaced struts wherein each said elongated member comprises a free end portion extending away from said second end portion.

19. The device of claim 18, wherein said first end portion further comprises:
a second set of spaced struts axially spaced from said plurality of said spaced struts of said second end portion, said second set of spaced struts being collapsible over a variable range of distance to accommodate for varying wall thicknesses of the tubular conduits being joined by anastomosis.

20. The device of claim 19, wherein an end of said second end portion maintains substantially the same angulation with respect to the normal after buckling of said spaced struts as before buckling.

21. The device of claim 19, wherein said first end portion maintains substantially the same angulation with respect to the normal after collapsing of said second set of spaced struts as before collapsing.

22. The device of claim 19, wherein said second set of struts begins collapsing after said struts of said second end portion have buckled.

23. The device of claim 19, wherein said second set of struts have a higher compression strength than said struts of said second end portion.

24. The device of claim 19, wherein said second set of struts are plastically deformed upon collapsing.

25. The device of claim 18, wherein an end of said second end portion maintains substantially the same angulation with respect to the normal after buckling of said spaced struts as before buckling.

26. The device of claim 18, wherein said first end portion maintains substantially the same angulation with respect to the normal after buckling of said spaced struts as before buckling.

27. The device of claim 18, wherein at least one of said plurality of spaced struts comprises a pair of strut portions of unequal length, wherein said at one strut comprising a unequal length strut portions, upon buckling orients at an angle to a normal to a longitudinal axis of said main body.

28. The device of claim 18, wherein said first end portion further comprises a first ring member angled with respect to the normal, wherein said plurality of members extending radially outwardly from said first end portion extend from said first ring member; and wherein said second end portion comprises a second ring member angled with respect to the normal, wherein said plurality of spaced struts extend from said second ring member toward said first ring member.

29. The device of claim 28, wherein said first and second rings are angled with respect to the normal by substantially the same degree of angulation.

30. The device of claim 28, wherein said plurality of spaced struts connect said second ring member with said first ring member.

31. The device of claim 28, further comprising a plurality of tines extending radially outwardly from said second end portion and adapted to mechanically engage an everted end of a first of the tubular fluid conduits.

32. The device of claim 18, wherein said elongated members extend substantially parallel to the longitudinal axis.

33. The device of claim 18, wherein each said elongated member comprises a weakened portion adapted to fail under tension before the remainder of said elongated member.

34. The device of claim 33, wherein said weakened portions are necked portions.

35. The device of claim 18, wherein each said free end portion extends beyond said first end portion.

36. The device of claim 18, wherein each said free end portion comprises an engagement portion adapted for engagement with a deployment device, for application of tension to said elongated member by the deployment device.

37. The device of claim 18, further comprising a plurality of tines extending radially outwardly from said second end portion.

38. The device of claim 37, wherein said plurality of tines extend from said spaced struts.

39. The device of claim 37, wherein said tines are graft tines adapted to pierce a side wall of one of the conduits to be joined by anastomosis.

40. The device of claim 18, wherein said main body defines an annular space which is configured to slide over the outer wall of one of the two conduits to be joined by anastomosis.

41. The device of claim 18, wherein the second end portion struts, upon buckling, are adapted to form a compression fit with said members extending radially outwardly from said first end portion to form a seal between an everted end of one of the tubular fluid conduits and an inner wall of a second of the tubular fluid conduits.

42. The device of claim 41, wherein said first and second end portions maintain substantially the same angulation with respect to the normal after buckling of said spaced struts as before buckling.

43. The device of claim 18, wherein said second end portion comprises an end angled with respect to the normal by an angle less than the angulation of said first end portion with respect to the normal.

44. The device of claim 43, wherein said end of said second end portion is adapted to collapse to a configuration which is angled to the normal at substantially the same angle as the angulation of said first end portion to the normal, prior to buckling of said struts.

45. A device for use in making an angled anastomosis between tubular fluid conduits in the body of a patient, said device comprising:
a unitary structure having a main body disposed annularly about a longitudinal axis and having first and second end portions each encircling an annulus that the longitudinal axis passes through and angled with respect to a normal to the longitudinal axis, said first end portion having a first end angled with respect to the normal to the longitudinal axis, with a location on said first end that is furthest from said normal to the longitudinal axis at a location passing through said main body being opposite to a location on said first end that is nearest to said normal to the longitudinal axis at said location passing through said main body;
a plurality of members extending radially outwardly from said first end portion; and
said second end portion having a plurality of spaced struts adapted to buckle in a radially outward direction upon axial compression of said device, wherein said struts are plastically deformed during buckling, wherein at least one of said plurality of spaced struts, upon buckling, buckles at a location along a length of said at least one strut that is different from a relative location at which at least another one of said struts buckles along a length of said at least another one of said struts, whereby said at least one strut orients at an angle in a first direction to the normal to the longitudinal axis of said main body, and said at least another one of said plurality of spaced struts, upon buckling, orients at an angle is a second direction, opposite to said first direction, to the normal to the longitudinal axis of said main body.

46. A device for use in making an angled anastomosis between tubular fluid conduits in the body of a patient, said device comprising:
a unitary structure having a main body disposed annularly about a longitudinal axis and having first and second end portions each encircling an annulus that the longitudinal axis passes through and angled with respect to a normal to the longitudinal axis, said first end portion having a first end angled with respect to the normal to the longitudinal axis, with a location on said first end that is furthest from said normal to the longitudinal axis at a location passing through said main body being opposite to a location on said first end that is nearest to said normal to the longitudinal axis at said location passing through said main body;
a plurality of members extending radially outwardly from said first end portion; and
said second end portion having a plurality of spaced struts adapted to buckle in a radially outward direction upon axial compression of said device, wherein said struts are plastically deformed during buckling, wherein at least one of said plurality of spaced struts, upon buckling, orients normal to the longitudinal axis of said main body.

47. A device for use in making an angled anastomosis between tubular fluid conduits in the body of a patient, said device comprising:
a unitary structure having a main body disposed annularly about a longitudinal axis and having first and second end portions each encircling an annulus that the longitudinal axis passes through and angled with respect to a normal to the longitudinal axis, said first end portion having a first end angled with respect to the normal to the longitudinal axis, with a location on said first end that is furthest from said normal to the longitudinal axis at a location passing through said main body being opposite to a location on said first end that is nearest to said normal to the longitudinal axis at said location passing through said main body;
a plurality of members extending radially outwardly from said first end portion; and
said second end portion having a plurality of spaced struts adapted to buckle in a radially outward direction upon axial compression of said device, wherein said struts are plastically deformed during buckling;
wherein said first end portion further comprises:
a second set of spaced struts axially spaced from said plurality of said spaced struts of said second end portion, said second set of spaced struts being collapsible over a variable range of distance to accommodate for varying wall thicknesses of the tubular conduits being joined by anastomosis; and
wherein said first end portion further comprises a first ring member angled with respect to the normal, wherein said plurality of members extending radially outwardly from said first end portion extend from said first ring member; and wherein said second end portion comprises a second ring member angled with respect to the normal; and further comprising a third ring member intermediate of said first and second ring members and angled with respect to the normal, wherein said plurality of spaced struts extend from said second ring member to said third ring member; and wherein said second set of spaced struts extend from said first ring member to said third ring member.

48. The device of claim 47, wherein said first, second and third rings are all angled with respect to the normal by substantially the same degree of angulation.

49. A device for use in making an angled anastomosis between tubular fluid conduits in the body of a patient, said device comprising:
- a unitary structure having a main body disposed annularly about a longitudinal axis and having first and second end portions each encircling an annulus that the longitudinal axis passes through and angled with respect to a normal to the longitudinal axis;
- said first end portion having:
  - a first end angled with respect to the normal to the longitudinal axis, with a location on said first end that is furthest from said normal to the longitudinal axis at a location passing through said main body being opposite to a location on said first end that is nearest to said normal to the longitudinal axis at said location passing through said main body;
  - a plurality of members extending radially outwardly from said first end portion; and
  - a first ring member angled with respect to the normal, wherein said plurality of members extending radially outwardly from said first end portion extend from said first ring member;
- and said second end portion having:
  - a plurality of spaced struts adapted to buckle in a radially outward direction upon axial compression of said device, wherein said struts are plastically deformed during buckling;
  - a plurality of tines extending radially outwardly from said second end portion and adapted to mechanically engage an everted end of a first of the tubular fluid conduits; and
  - a second ring member angled with respect to the normal, wherein said plurality of spaced struts extend from said second ring member toward said first ring member;
- a ring portion connected to said second ring member to form a second end of said device with said second ring portion, said second end being angled with respect to the normal by an angle less than the angulation of said first end portion with respect to the normal.

50. The device of claim 49, further comprising struts interconnecting said ring portion and said second ring member, said struts being adapted to collapse before the buckling of said plurality of spaced struts adapted to buckle in a radially outward direction.

51. The device of claim 49, wherein, upon collapse of said struts interconnecting said ring portion and said second ring member, said second end is oriented at substantially the same angle of orientation to the normal as said first end portion.

52. A device for use in making an angled anastomosis between tubular fluid conduits in the body of a patient, said device comprising:
- a unitary structure having a main body disposed annularly about a longitudinal axis and having first and second end portions each encircling an annulus that the longitudinal axis passes through and angled with respect to a normal to the longitudinal axis, said first end portion having a first end angled with respect to the normal to the longitudinal axis, with a location on said first end that is furthest from said normal to the longitudinal axis at a location passing through said main body being opposite to a location on said first end that is nearest to said normal to the longitudinal axis at said location passing through said main body;
- a plurality of members extending radially outwardly from said first end portion; and
- said second end portion having a plurality of spaced struts adapted to buckle in a radially outward direction upon axial compression of said device, wherein said struts are plastically deformed during buckling and wherein strut portions of said struts are formed of varying lengths, depending upon the relative position of each said strut in said device.

53. A device for use in making an angled anastomosis between first and second tubular fluid conduits in the body of a patient, said device comprising:
- a unitary structure having a main body disposed annularly about a longitudinal axis, having a proximal end portion with a proximal end, and a distal end portion with a distal end, and adapted for passing the first tubular conduit through an annulus defined by the main body;
- an exterior of said main body configured to be inserted through an opening in the second tubular conduit;
- at least one first member extending radially from said proximal end portion and angled toward a proximal direction of said device, relative to said longitudinal axis, and at least one second member extending radially from said proximal end portion and angled toward a distal direction of said device, relative to said longitudinal axis, said members extending from said proximal end portion configured to abut against an external wall of the second conduit upon angulation of said main body with respect to a wall of the second tubular conduit;
- said distal end portion being configured to buckle in response to axial compression of said device, wherein said distal end portion plastically deforms and is incapable of passing through said opening after buckling and exerts a compressive force between the first conduit and the wall of the second conduit upon buckling, while maintaining the angled configuration of the main body with respect to the second conduit; and
- locking members fixed to said distal end portion and slidably received by said proximal end portion, wherein, upon buckling of said distal end portion, free ends of said locking members slide to extend proximally of said proximal end portion.

54. An anastomosis device comprising:
- a unitary structure having a main body having an outside diameter adapted to pass through and form a close fit with an opening formed in a wall of a conduit to be joined by anastomosis;
- said main body defining an annulus having an inside diameter, said annulus extending longitudinally through said body along a longitudinal axis thereof;
- said body having proximal and distal end portions angled at non-zero angles with respect to a normal to the longitudinal axis, said proximal and distal end portions having a proximal and distal end, respectively, said distal ends being uniformly angled with respect to said normal and said proximal ends being uniformly angled with respect to said normal;
- an extension portion extending from said proximal end portion, having a length sufficient to span the length of said main body, and configured to be incapable of passing through the opening;

conduit retainers on said distal end portion adapted to retain a free end portion of a conduit having been passed through said annulus and everted over said proximal end portion; and locking members fixed to said distal end portion and slidably received by said proximal end portion, wherein, upon buckling of said distal end portion, free ends of said locking members slide to extend proximally of said proximal end portion.

55. A device for use in making an angled anastomosis between tubular fluid conduits in the body of a patient, said device comprising:

a unitary structure having a main body disposed annularly about a longitudinal axis and having first and second end portions each encircling an annulus that the longitudinal axis passes through and angled with respect to a normal to the longitudinal axis, said first end portion having a first end angled with respect to the normal to the longitudinal axis, with a location on said first end that is furthest from said normal to the longitudinal axis at a location passing through said main body being opposite to a location on said first end that is nearest to said normal to the longitudinal axis at said location passing through said main body;

a plurality of members extending radially outwardly from said first end portion;

a plurality of spaced locking tines integral with second end portion and slidably connecting with said first end portion; and said second end portion having a plurality of spaced struts adapted to buckle in a radially outward direction upon axial compression of said device, wherein said struts are plastically deformed during buckling.

56. The device of claim 55, wherein upon compression of said device, said locking tines slide with respect to said first end portion and extend beyond said first end portion, said locking tines being adapted to be bent over to lock the relative positions of said first and second end portions.

57. The device of claim 55, wherein said first end portion further comprises a plurality of eyelets axially aligned with said locking tines, through which said locking tines are slidably connected to said first end portion.

\* \* \* \* \*